United States Patent
Rosenbaum et al.

(10) Patent No.: US 10,752,914 B2
(45) Date of Patent: Aug. 25, 2020

(54) METHODS, COMPOSITIONS AND CELLS FOR PREPARING SURFACTANT PROTEIN D (SP-D)

(71) Applicants: Airway Therapeutics, Inc., Cincinnati, OH (US); Glycotope GmbH, Berlin (DE)

(72) Inventors: Jan Susan Rosenbaum, Cincinnati, OH (US); Frederick Gyapon Quast, Berlin (DE); Matthias Kaup, Berlin (DE); Lars Stöckl, Berlin (DE)

(73) Assignees: Airway Therapeutics, Inc., Cinncinnati, OH (US); Glycotope GmbH, Berlin (DE)

( * ) Notice: Subject to any disclaimer, the term of this patent is extended or adjusted under 35 U.S.C. 154(b) by 49 days.

(21) Appl. No.: 16/121,039

(22) Filed: Sep. 4, 2018

(65) Prior Publication Data

US 2019/0071693 A1     Mar. 7, 2019

Related U.S. Application Data

(60) Provisional application No. 62/614,758, filed on Jan. 8, 2018, provisional application No. 62/554,825, filed on Sep. 6, 2017.

(51) Int. Cl.
| | |
|---|---|
| *C07K 14/785* | (2006.01) |
| *C12N 15/85* | (2006.01) |
| *C12N 5/09* | (2010.01) |
| *C12N 9/06* | (2006.01) |
| *C07K 14/725* | (2006.01) |

(52) U.S. Cl.
CPC .......... *C12N 15/85* (2013.01); *C07K 14/7051* (2013.01); *C07K 14/785* (2013.01); *C12N 5/0694* (2013.01); *C12N 9/003* (2013.01); *C12Y 105/01003* (2013.01); *C07K 2319/00* (2013.01); *C12N 2015/8518* (2013.01)

(58) Field of Classification Search
None
See application file for complete search history.

(56) References Cited

U.S. PATENT DOCUMENTS

| | | |
|---|---|---|
| 8,609,370 B2 | 12/2013 | Goletz et al. |
| 9,051,356 B2 | 6/2015 | Goletz et al. |
| 9,359,427 B2 | 6/2016 | Stahn |
| 2008/0226681 A1 | 9/2008 | Goletz et al. |
| 2008/0242615 A1 | 10/2008 | Ikegami et al. |
| 2011/0277165 A1 | 11/2011 | Popi |
| 2012/0220531 A1 | 8/2012 | Whitsett et al. |
| 2013/0330768 A1 | 12/2013 | Stahn |
| 2015/0353959 A1 | 12/2015 | Goletz et al. |
| 2015/0368363 A1 | 12/2015 | Goletz et al. |
| 2016/0331844 A1 | 11/2016 | Fotin-Mleczek et al. |
| 2016/0333074 A1 | 11/2016 | Van Eijk et al. |
| 2017/0080103 A1 | 3/2017 | Ariaans et al. |
| 2019/0071694 A1 | 3/2019 | Rosenbaum et al. |

FOREIGN PATENT DOCUMENTS

| | | |
|---|---|---|
| WO | WO 2015/011266 | 1/2015 |
| WO | WO 2017/162733 | 9/2017 |

OTHER PUBLICATIONS

Leth-Larsen, R., et al. 2005 The Journal of Immunology 174: 1532-1538. (Year: 2005).*
UniProKB P35247 SFTPD_Human amino acid sequence, available Feb. 1, 1994. (Year: 1994).*
Swiech, K., et al. 2012 Protein Expression and Purification 84: 147-153. (Year: 2012).*
Arroyo et al., Supramolecular Assembly of Human Pulmonary Surfactant Protein SP-D. J Mol Biol. (2018) 430(10):1495-1509.
Clark et al., Structural requirements for SP-D function in vitro and in vivo: therapeutic potential of recombinant SP-D. Immunobiology (2002) 205(4-5):619-631.
Clements J.A., Functions of the alveolar lining, Am Rev Respir Dis (1977) 115(6 Pt 2):67-71.
Crouch et al., Molecular structure of pulmonary surfactant protein D (SP-D). J Biol Chem. (1994) 269(25):17311-17319.
Crouch E.C., Surfactant protein-D and pulmonary host defense. Respir Res. (2000) 1(2):93-108.
Crouch et al., Contributions of phenylalanine 335 to ligand recognition by human surfactant protein D: ring interactions with SP-D ligands. J Biol Chem., (2006) 281(26):18008-18014.
Dodagatta-Marri et al., Purification of surfactant protein D (SP-D) from pooled amniotic fluid and bronchoalveolar lavage. Methods Mol Biol. (2014) 1100:273-290.
Griese M., Pulmonary surfactant in health and human lung diseases: State of the art, Eur Respir J (1999) 13:1455-1476.
Håkansson et al., Collectin structure: a review. Protein Sci. (2000) 9:1607-1617.
Ikegami et al., Intratracheal Recombinant Surfactant Protein D Prevents Endotoxin Shock in the Newborn Preterm Lamb. Am J Respir Crit Care Med. (2006) 173(12):1342-1347.
Manning et al., AF4-MALLS Analysis of Surfactant Protein-D (SP-D), University of South Carolina—19th International Symposium of Field- and Flow-based Seperations; May 14-17, 2018, 2 pages.
Robertson et al., Principles of surfactant replacement, Biochim Biophys Acta (1998) 1408:346-361.
Salgado et al., Comparative Evaluation of Heterologous Production Systems for Recombinant Pulmonary Surfactant Protein D. Front Immunol. (2014) 5:623.

(Continued)

*Primary Examiner* — Marsha Tsay
(74) *Attorney, Agent, or Firm* — Knobbe, Martens, Olson & Bear LLP

(57) ABSTRACT

Some embodiments of the methods and compositions provided herein relate to the preparation surfactant protein-D (SP-D). Some embodiments include the expression of human SP-D in certain cell lines, and the purification of human SP-D from such cell lines. Some embodiments include the preparation of certain oligomeric forms of human SP-D.

20 Claims, 12 Drawing Sheets

Specification includes a Sequence Listing.

(56) References Cited

OTHER PUBLICATIONS

Sato et al., Surfactant Protein-D Inhibits Lung Inflammation Caused by Ventilation in Premature Newborn Lambs. Am J Respir Crit Care Med. (2010) 181(10):1098-1105.
Strong et al., A novel method of purifying lung surfactant proteins A and D from the lung lavage of alveolar proteinosis patients and from pooled amniotic fluid. J Immunol Methods. (1998) 220(1-2):139-149.
White et al., Multimerization of surfactant protein D, but not its collagen domain, is required for antiviral and opsonic activities related to influenza virus. J Immunol. (2008) 181(11):7936-7943.
Yamazoe et al., Pulmonary surfactant protein D inhibits lipopolysaccharide (LPS)-induced inflammatory cell responses by altering LPS binding to its receptors. J Biol Chem. (2008) 283(51):35878-35888.
Zhang et al., Activity of pulmonary surfactant protein-D (SP-D) in vivo is dependent on oligomeric structure. J Biol Chem (2001) 276(22):19214-19219.
Zuo et al., Current perspective in pulmonary surfactant—Inhibition, enhancement and evaluation, Biochim Biophys Acta (2008) 1778:1947-1977.
Ferrara et al., Unique carbohydrate-carbohydrate interactions are required for high affinity binding between FcγRIII and antibodies lacking core fucose. PNAS U.S.A. (2011) 108(31):12669-12674.
Rouwendal et al., A comparison of anti-HER2 IgA and IgG1 in vivo efficacy is facilitated by high N-glycan sialylation of the IgA. mAbs (2016) 8(1):74-86.
Carreto-Binaghi, et al, Surfactant proteins, SP-A and SP-D, in respiratory fungal infections: their role in the inflammatory response, Respiratory Research (2016) 17:66.
Hartshorn et al., Interactions of recombinant human pulmonary surfactant protein D and SP-D multimers with influenza A. Am J Physiol. (1996) 271(5Pt1):L753-L762.
Jenkins, et al. Getting the glycosylation right: Implications for the biotechnology industry, Nature Biotechnology (1996) 14:975-981.

\* cited by examiner

SEQUENCE LISTING

<160> NUMBER OF SEQ ID NOS: 10

<210> SEQ ID NO 1
<211> LENGTH: 1150
<212> TYPE: DNA
<213> ORGANISM: homo sapiens

<400> SEQUENCE: 1

```
aagcttgcca ccatgctgct gtttctgctg agcgccctgg tgctgctgac acagcctctg      60
ggctatctgg aagccgagat gaagacctac agccaccgga ccatgcccag cgcctgtacc     120
ctcgtgatgt gcagcagcgt ggaaagcggc ctgcctggca gagatggcag ggatggaaga     180
```

```
gagggcccca gaggcgagaa gggcgatcct ggactgcctg cgctgcagg gcaggctgga      240 atgcctggac aggctggacc tgtgggcccc aagggcgata tggctctgt gggagagcct      300 ggccctaagg gggatacagg cccttctgga cctcctggac cacctggcgt gccaggacct      360
gctggaagag aaggacctct gggcaagcag ggcaacatcg cccctcaggg aaagccagga      420
ccaaagggcg aggccggacc caaaggcgaa gtgggagcac ctggcatgca gggaagtgcc      480
ggcgctagag gactggctgg cccaaaaggc gaaggggga tgcctggcga agaggcgtg       540 cccggaaata ctggcgccgc tggatctgct ggcgccatgg gacctcaggg atctccaggc    600
gcaagaggcc ctccaggcct gaaaggcgac aaaggcatcc ccggcgataa gggcgctaag    660
ggcgaatccg gcctgccaga tgtggccagc ctgagacagc aggtggaagc tctccagggc    720
caggtgcagc atctccaggc tgccttcagc cagtacaaga aggtggaact gttccccaac    780
ggccagagcg tgggcgagaa gatctttaag accgccggct tcgtgaagcc cttcaccgag    840
gctcagctgt gtgtaccca ggctggcgga cagctggcct ctcctagatc tgccgccgaa     900
aatgccgctc tccagcagct ggtggtggcc aagaatgagg ccgccttcct gagcatgacc    960
gacagcaaga ccgagggcaa gttcacctac cccaccggcg agtccctggt gtacagcaat    1020
tgggcccctg gcgagcccaa cgatgatggc ggctctgagg actgcgtgga aatcttcacc    1080
aacggcaagt ggaacgaccg ggcctgtggc gagaaaagac tggtcgtgtg cgagttctga    1140
agggtctaga                                                            1150
```

<210> SEQ ID NO 2
<211> LENGTH: 1138
<212> TYPE: DNA
<213> ORGANISM: homo sapiens

<400> SEQUENCE: 2

```
gccaccatgc tgctgtttct gctgagcgcc ctggtgctgc tgacacagcc tctgggctat       60
ctggaagccg agatgaagac ctacagccac cggaccatgc ccagcgcctg taccctcgtg      120
atgtgcagca gcgtggaaag cggcctgcct ggcagagatg gcagggatgg aagagggc       180 cccagaggcg agaagggcga tcctggactg cctggcgctg cagggcaggc tggaatgcct     240
ggacaggctg gacctgtggg ccccaagggc gataatggct ctgtgggaga gcctggccct    300
aagggggata caggcccttc tggacctcct ggaccacctg gcgtgccagg acctgctgga    360
agagaaggac ctctgggcaa gcagggcaac atcggccctc agggaaagcc aggaccaaag    420 ggcgaggcc gacccaaagg cgaagtggga gcacctggca tgcagggaag tgccggcgct     480
agaggactgg ctggcccaaa aggcgaaagg ggagtgcctg gcgaaagagg cgtgcccgga    540
aatactggcg ccgctggatc tgctggcgcc atgggacctc agggatctcc aggcgcaaga    600
ggccctccag gcctgaaagg cgacaaaggc atccccggcg ataagggcgc taagggcgaa    660
tccggcctgc cagatgtggc cagcctgaga cagcaggtgg aagctctcca gggccaggtg    720
cagcatctcc aggctgcctt cagccagtac aagaaggtgg aactgttccc caacggccag    780
agcgtgggcg agaagatctt taagaccgcc ggcttcgtga agcccttcac cgaggctcag    840
ctgctgtgta cccaggctgg cggacagctg gcctctccta gatctgccgc cgaaaatgcc    900
gctctccagc agctggtggt ggccaagaat gaggccgcct tcctgagcat gaccgacagc    960
aagaccgagg gcaagttcac ctaccccacc ggcgagtccc tggtgtacag caattgggcc    1020
cctggcgagc ccaacgatga tggcggctct gaggactgcg tggaaatctt caccaacggc    1080
```
aagtggaacg accgggcctg tggcgagaaa agactggtcg tgtgcgagtt ctgaaggg         1138

<210> SEQ ID NO 3
<211> LENGTH: 60
<212> TYPE: DNA
<213> ORGANISM: homo sapiens

<400> SEQUENCE: 3
atgctgctgt tctgctgag cgccctggtg ctgctgacac agcctctggg ctatctggaa        60

<210> SEQ ID NO 4
<211> LENGTH: 376
<212> TYPE: PRT
<213> ORGANISM: homo sapiens

<400> SEQUENCE: 4

Met Leu Leu Phe Leu Leu Ser Ala Leu Val Leu Leu Thr Gln Pro Leu
1               5                   10                  15

Leu Gly Tyr Leu Glu Ala Glu Met Lys Thr Tyr Ser His Arg Thr Met
            20                  25                  30

Pro Ser Ala Cys Thr Leu Val Met Cys Ser Ser Val Glu Ser Gly Leu
        35                  40                  45

Pro Gly Arg Asp Gly Arg Asp Gly Arg Glu Gly Pro Arg Gly Glu Lys
    50                  55                  60

Gly Asp Pro Gly Leu Pro Gly Ala Ala Gly Gln Ala Gly Met Pro Gly
65                  70                  75                  80

Gln Ala Gly Pro Val Gly Pro Lys Gly Asp Asn Gly Ser Val Gly Glu
                85                  90                  95

Pro Gly Pro Lys Gly Asp Thr Gly Pro Ser Gly Pro Pro Gly Pro Pro
            100                 105                 110

Gly Val Pro Gly Pro Ala Gly Arg Glu Gly Pro Leu Gly Lys Gln Gly
        115                 120                 125

Asn Ile Gly Pro Gln Gly Lys Pro Gly Pro Lys Gly Glu Ala Gly Pro
    130                 135                 140

Lys Gly Glu Val Gly Ala Pro Gly Met Gln Gly Ser Ala Gly Ala Arg
145                 150                 155                 160

Gly Leu Ala Gly Pro Lys Gly Glu Arg Gly Val Pro Gly Glu Arg Gly
                165                 170                 175

Val Pro Gly Asn Thr Gly Ala Ala Gly Ser Ala Gly Ala Met Gly Pro
            180                 185                 190

Gln Gly Ser Pro Gly Ala Arg Gly Pro Pro Gly Leu Lys Gly Asp Lys
        195                 200                 205

Gly Ile Pro Gly Asp Lys Gly Ala Lys Gly Glu Ser Gly Leu Pro Asp
    210                 215                 220

Val Ala Ser Leu Arg Gln Gln Val Glu Ala Leu Gln Gly Gln Val Gln
225                 230                 235                 240

His Leu Gln Ala Ala Phe Ser Gln Tyr Lys Lys Val Glu Leu Phe Pro
                245                 250                 255

Asn Gly Gln Ser Val Gly Glu Lys Ile Phe Lys Thr Ala Gly Phe Val
            260                 265                 270

Lys Pro Phe Thr Glu Ala Gln Leu Leu Cys Thr Gln Ala Gly Gly Gln
        275                 280                 285

Leu Ala Ser Pro Arg Ser Ala Ala Glu Asn Ala Ala Leu Gln Gln Leu
    290                 295                 300

Val Val Ala Lys Asn Glu Ala Ala Phe Leu Ser Met Thr Asp Ser Lys
305                 310                 315                 320

```
Thr Glu Gly Lys Phe Thr Tyr Pro Thr Gly Glu Ser Leu Val Tyr Ser
            325                 330                 335

Asn Trp Ala Pro Gly Glu Pro Asn Asp Gly Ser Glu Asp Cys
            340                 345                 350

Val Glu Ile Phe Thr Asn Gly Lys Trp Asn Asp Arg Ala Cys Gly Glu
            355                 360                 365

Lys Arg Leu Val Val Cys Glu Phe
        370                 375

<210> SEQ ID NO 5
<211> LENGTH: 21
<212> TYPE: PRT
<213> ORGANISM: homo sapiens

<400> SEQUENCE: 5

Met Leu Leu Phe Leu Leu Ser Ala Leu Val Leu Leu Thr Gln Pro Leu
1               5                   10                  15

Leu Gly Tyr Leu Glu
            20

<210> SEQ ID NO 6
<211> LENGTH: 1153
<212> TYPE: DNA
<213> ORGANISM: homo sapiens

<400> SEQUENCE: 6
aagcttgcca ccatggcctg ccccggattt ctgtgggccc tcgtgatcag cacctgtctg      60
gaattcagca tggccgccga gatgaagacc tacagccacc ggacaatgcc cagcgcctgc    120
accctcgtga tgtgcagctc tgtggaaagc ggcctgcccg cagagatgg cagggatgga     180 agagagggac ccagaggcga agggcgat cctggactgc ctggcgctgc agggcaggct       240
ggaatgcctg acaggctgg acctgtgggc cccaagggcg ataatggctc tgtgggagag      300
cctggcccta aggggatac aggcccttct ggacctcctg gaccacctgg cgtgccagga      360
cctgctggaa gagaaggacc tctgggcaag cagggcaaca tcggccctca gggaaagcca    420
ggaccaaagg gcgaggccgg acccaaaggc gaagtgggag cacctggcat gcagggaagt    480
gccggcgcta gaggactggc tggcccaaaa ggcgaaaggg gagtgcctgg cgaaagaggc    540
gtgcccggaa atactggcgc cgctggatct gctggcgcca tgggacctca gggatctcca    600
ggcgcaagag ccctccagg cctgaaaggc gacaaaggca tccccggcga taagggcgct     660
aagggcgaat ccggcctgcc agatgtggcc agcctgagac agcaggtgga agctctccag    720
ggccaggtgc agcatctcca ggctgccttc agccagtaca gaaggtgga actgttcccc     780 aacggccaga gcgtgggcga aagatctttt aagaccgccg gcttcgtgaa gcccttcacc    840
gaggctcagc tgctgtgtac ccaggctggc ggacagctgg cctctcctag atctgccgcc    900
gaaaatgccg ctctccagca gctggtggtg ccaagaatg aggccgcctt cctgagcatg      960
accgacagca agaccgaggg caagttcacc taccccaccg gcgagtccct ggtgtacagc    1020
aattgggccc ctggcgagcc caacgatgat ggcggctctg aggactgcgt ggaaatcttc    1080
accaacggca gtggaacga ccgggcctgt ggcgagaaaa gactggtcgt gtgcgagttc     1140
tgaagggtct aga                                                      1153

<210> SEQ ID NO 7
<211> LENGTH: 1141
<212> TYPE: DNA
```

<213> ORGANISM: homo sapiens

<400> SEQUENCE: 7

```
gccaccatgg cctgccccgg atttctgtgg ccctcgtga tcagcacctg tctggaattc      60
agcatggccg ccgagatgaa gacctacagc caccggacaa tgcccagcgc ctgcaccctc    120
gtgatgtgca gctctgtgga aagcggcctg ccggcagag atggcaggga tggaagagag     180
ggacccagag gcgagaaggg cgatcctgga ctgcctggcg ctgcagggca ggctggaatg    240
cctggacagg ctggacctgt gggccccaag ggcgataatg gctctgtggg agagcctggc    300
cctaagggg atacaggccc ttctggacct cctggaccac ctggcgtgcc aggacctgct    360
ggaagagaag gacctctggg caagcagggc aacatcggcc ctcagggaaa gccaggacca    420
aagggcgagg ccggacccaa aggcgaagtg gagcacctg gcatgcaggg aagtgccggc     480
gctagaggac tggctggccc aaaaggcgaa agggagtgc ctggcgaaag aggcgtgccc     540
ggaaatactg gcgccgctgg atctgctggc gccatgggac ctcagggatc tccaggcgca    600
agaggccctc caggcctgaa aggcgacaaa ggcatcccg gcgataaggg cgctaagggc    660
gaatccggcc tgccagatgt ggccagcctg agacagcagg tggaagctct ccagggccag    720
gtgcagcatc tccaggctgc cttcagccag tacaagaagg tggaactgtt ccccaacggc    780
cagagcgtgg gcgagaagat cttaagacc gccggcttcg tgaagccctt caccgaggct    840
cagctgctgt gtacccaggc tggcggacag ctggcctctc ctagatctgc cgccgaaaat    900
gccgctctcc agcagctggg ggtggccaag aatgaggccg ccttcctgag catgaccgac    960
agcaagaccg agggcaagtt cacctacccc accggcgagt ccctggtgta cagcaattgg   1020
gccctggcg agcccaacga tgatggcggc tctgaggact gcgtggaaat cttcaccaac   1080
ggcaagtgga acgaccgggc ctgtggcgag aaaagactgg tcgtgtgcga gttctgaagg   1140
g                                                                  1141
```

<210> SEQ ID NO 8
<211> LENGTH: 63
<212> TYPE: DNA
<213> ORGANISM: homo sapiens

<400> SEQUENCE: 8

```
atggcctgcc ccggatttct gtgggccctc gtgatcagca cctgtctgga attcagcatg     60
gcc                                                                  63
```

<210> SEQ ID NO 9
<211> LENGTH: 376
<212> TYPE: PRT
<213> ORGANISM: homo sapiens

<400> SEQUENCE: 9

```
Met Ala Cys Pro Gly Phe Leu Trp Ala Leu Val Ile Ser Thr Cys Leu
1               5                   10                  15

Glu Phe Ser Met Ala Ala Glu Met Lys Thr Tyr Ser His Arg Thr Met
            20                  25                  30

Pro Ser Ala Cys Thr Leu Val Met Cys Ser Ser Val Glu Ser Gly Leu
        35                  40                  45

Pro Gly Arg Asp Gly Arg Asp Gly Arg Glu Gly Pro Arg Gly Glu Lys
    50                  55                  60

Gly Asp Pro Gly Leu Pro Gly Ala Ala Gly Gln Ala Gly Met Pro Gly
65                  70                  75                  80
```

Gln Ala Gly Pro Val Gly Pro Lys Gly Asp Asn Gly Ser Val Gly Glu
                85                  90                  95

Pro Gly Pro Lys Gly Asp Thr Gly Pro Ser Gly Pro Pro Gly Pro Pro
            100                 105                 110

Gly Val Pro Gly Pro Ala Gly Arg Glu Gly Pro Leu Gly Lys Gln Gly
        115                 120                 125

Asn Ile Gly Pro Gln Gly Lys Pro Gly Pro Lys Gly Glu Ala Gly Pro
130                 135                 140

Lys Gly Glu Val Gly Ala Pro Gly Met Gln Gly Ser Ala Gly Ala Arg
145                 150                 155                 160

Gly Leu Ala Gly Pro Lys Gly Glu Arg Gly Val Pro Gly Glu Arg Gly
                165                 170                 175

Val Pro Gly Asn Thr Gly Ala Ala Gly Ser Ala Gly Ala Met Gly Pro
            180                 185                 190

Gln Gly Ser Pro Gly Ala Arg Gly Pro Pro Gly Leu Lys Gly Asp Lys
        195                 200                 205

Gly Ile Pro Gly Asp Lys Gly Ala Lys Gly Glu Ser Gly Leu Pro Asp
210                 215                 220

Val Ala Ser Leu Arg Gln Gln Val Glu Ala Leu Gln Gly Gln Val Gln
225                 230                 235                 240

His Leu Gln Ala Ala Phe Ser Gln Tyr Lys Lys Val Glu Leu Phe Pro
                245                 250                 255

Asn Gly Gln Ser Val Gly Glu Lys Ile Phe Lys Thr Ala Gly Phe Val
            260                 265                 270

Lys Pro Phe Thr Glu Ala Gln Leu Leu Cys Thr Gln Ala Gly Gly Gln
        275                 280                 285

Leu Ala Ser Pro Arg Ser Ala Ala Glu Asn Ala Ala Leu Gln Gln Leu
290                 295                 300

Val Val Ala Lys Asn Glu Ala Ala Phe Leu Ser Met Thr Asp Ser Lys
305                 310                 315                 320

Thr Glu Gly Lys Phe Thr Tyr Pro Thr Gly Glu Ser Leu Val Tyr Ser
                325                 330                 335

Asn Trp Ala Pro Gly Glu Pro Asn Asp Asp Gly Gly Ser Glu Asp Cys
            340                 345                 350

Val Glu Ile Phe Thr Asn Gly Lys Trp Asn Asp Arg Ala Cys Gly Glu
        355                 360                 365

Lys Arg Leu Val Val Cys Glu Phe
370                 375

<210> SEQ ID NO 10
<211> LENGTH: 21
<212> TYPE: PRT
<213> ORGANISM: homo sapiens

<400> SEQUENCE: 10

Met Ala Cys Pro Gly Phe Leu Trp Ala Leu Val Ile Ser Thr Cys Leu
1               5                   10                  15

Glu Phe Ser Met Ala
            20

METHODS, COMPOSITIONS AND CELLS FOR PREPARING SURFACTANT PROTEIN D (SP-D)

CROSS-REFERENCE TO RELATED APPLICATIONS

This application claims priority to U.S. Prov. App. No. 62/614,758 filed Jan. 8, 2018 entitled "METHODS, COMPOSITIONS AND CELLS FOR PREPARING SURFACTANT PROTEIN D (SP-D)", and to U.S. Prov. App. No. 62/554,825 filed Sep. 6, 2017 entitled "METHODS, COMPOSITIONS AND CELLS FOR PREPARING SURFACTANT PROTEIN D (SP-D)", which are each incorporated by reference in its entirety.

REFERENCE TO SEQUENCE LISTING

The present application is being filed along with a Sequence Listing in electronic format. The Sequence Listing is provided as a file entitled AIRWY007ASEQ, created Aug. 31, 2018, which is approximately 13 Kb in size. The information in the electronic format of the Sequence Listing is incorporated herein by reference in its entirety

FIELD OF THE INVENTION

Some embodiments of the methods and compositions provided herein relate to the preparation of surfactant protein-D (SP-D). Some embodiments include the expression of human SP-D in certain cell lines, and the purification of human SP-D from such cell lines. Some embodiments include the preparation of certain oligomeric forms of human SP-D.

BACKGROUND OF THE INVENTION

Mammalian pulmonary surfactant is a mixture of proteins (10%) and lipids (90%) including the major lipid component dipalmitoylphosphatidylcholine (Zuo Y Y, et al., Biochim Biophys Acta (2008) 1778:1947-77). The main function of the pulmonary surfactant is to ensure minimal surface tension within the lung to avoid collapse during respiration. Furthermore, by interacting with inhaled pathogens, the pulmonary surfactant also participates in host defense (Clements J A. Am Rev Respir Dis (1977) 115:67-71). Pulmonary surfactant deficiency is, therefore, associated with pulmonary diseases such as asthma, bronchiolitis, respiratory distress syndrome (RDS), cystic fibrosis, and pneumonia (Griese M. Eur Respir J (1999) 13:1455-76). Surfactant formulations are indicated for the treatment of RDS, which affects ~1.5 million premature babies globally every year. Respiratory distress syndrome is a major pulmonary surfactant deficiency disease caused by the structural immaturity of the lungs in premature infants, which makes it difficult to breathe, inhibits gas exchange, and promotes alveolar collapse (Notter R H. Lung Surfactants. Basic Science and Clinical Applications. New York, N.Y.: Marcel Dekker Inc.). However, treatment becomes more difficult if the lungs are infected or if there are inflammatory or oxidative complications, because current surfactant preparations lack surfactant protein D (SP-D). The successful treatment of complex pulmonary diseases, therefore, requires the production of surfactant formulations whose composition matches natural pulmonary surfactant as closely as possible (Robertson B, et al., Biochim Biophys Acta (1998) 1408:346-61).

SP-D has a role in the pulmonary innate immune system by providing anti-inflammatory and antimicrobial activities that address chronic pulmonary diseases such as asthma, cystic fibrosis, and smoking-induced emphysema (Clark H, et al., Immunobiology (2002) 205:619-31). Data based on premature newborn lambs suggest that the administration of ~2-3 mg/kg of recombinant human SP-D in combination with 100 mg/kg Survanta® (a natural surfactant available in USA) is more effective than Survanta® alone for the prevention of endotoxin shock and the reduction of lung inflammation caused by ventilation (Ikegami M, et al., Am J Respir Crit Care Med (2006) 173:1342-7; Sato A, et al., Am J Respir Crit Care Med (2010) 181:1098-105).

Traditionally, SP-D has been isolated from the supernatant of bronchoalveolar lavage or amniotic fluid, but most SP-D is lost during purification, in part due to the hydrophilic properties of SP-D (Dodagatta-Marri E, et al., Methods Mol Biol (2014) 100:273-90). The use of natural SP-D to supplement pulmonary surfactant formulations can ensure therapeutic efficiency because higher-order multimerization in the endogenous surfactant increases the number of SP-D-binding sites to carbohydrate ligands on the surface of pathogens, achieving potent bacterial and viral agglutination effects (White M, et al., J Immunol (2008) 181:7936-43). The appropriate oligomerization state is also required for receptor recognition and receptor-mediated signal transduction for modulation of the host immune response (Yamoze M et al., J Biol Chem (2008) 283:35878-35888) as well as for maintenance of surfactant homeostasis (Zhang L et al., J Biol Chem (2001) 276:19214-19219).

The low SP-D yields and variable oligomerization states make it difficult to use natural sources for the production of pharmaceutical SP-D (Strong P, et al., J Immunol Methods (1998) 220:139-49). To overcome some of these limitations, recombinant SP-D can be produced in microbes or mammalian cell lines, potentially offering a large-scale platform for the production of homogeneous recombinant SP-D formulations. However, it is challenging to express recombinant human SP-D (rhSP-D) to levels sufficient for a commercial campaign in commonly used mammalian cell lines because the protein is not synthesized efficiently and yields are typically <2 mg of purified protein per liter. Although yields tend to be higher in non-mammalian systems, expression of only a truncated variant of SP-D has been attempted in systems such as yeast or bacteria which have the disadvantage of either not producing the glycosylated form of the protein, or not producing the protein with a human glycosylation pattern (Salgado D, et al., Front Immunol (2014) 5:623, doi: 10.3389/fimmu.2014.00623). Furthermore, it has not been possible to date to control the variability in oligomerization states seen with recombinant and natural human SP-D. Unless the expression system can reproducibly produce rhSP-D with consistently stably levels of the higher-order multimerization states observed in natural SP-D, there is a potential for reduced efficacy of such preparations.

SUMMARY OF THE INVENTION

Some embodiments of the methods and compositions provided herein include a method for producing a human surfactant protein D (SP-D) polypeptide composition comprising: (a) introducing a polynucleotide encoding the SP-D polypeptide into a human mammalian cell; (b) culturing the cell under conditions in which the SP-D polypeptide is expressed; and (c) isolating the expressed SP-D polypeptide from the cell.

In some embodiments, the cell is derived from a human myeloid leukemia cell. In some embodiments, the cell is selected from the group consisting of NM-H9D8, NM-H9D8-E6Q12, and NM-F9. In some embodiments, the cell is a NM-H9D8 cell.

In some embodiments, the polynucleotide encodes a wild type SP-D polypeptide leader sequence.

In some embodiments, the polynucleotide comprises SEQ ID NO:03.

In some embodiments, the polynucleotide comprises SEQ ID NO:02.

In some embodiments, the polynucleotide encodes a polypeptide having an amino acid sequencing comprising SEQ ID NO:05.

In some embodiments, the polynucleotide encodes a polypeptide having an amino acid sequencing comprising SEQ ID NO:04.

In some embodiments, the polynucleotide encodes a wild type T-cell receptor (TCR) polypeptide leader sequence.

In some embodiments, the polynucleotide comprises SEQ ID NO:08.

In some embodiments, the polynucleotide comprises SEQ ID NO:07.

In some embodiments, the polynucleotide encodes a polypeptide having an amino acid sequencing comprising SEQ ID NO:10.

In some embodiments, the polynucleotide encodes a polypeptide having an amino acid sequencing comprising SEQ ID NO:09.

In some embodiments, the SP-D polypeptide comprises a residue at a polymorphic position, wherein the residue is selected from the group consisting of Met11/31, Thr160/180, Ser 270/290, and Ala 286/306. In some embodiments, the SP-D polypeptide comprises Met11/31. In some embodiments, the SP-D polypeptide comprises Met11/31, Thr160/180, Ser 270/290, and Ala 286/306.

Some embodiments also include isolating a population of the expressed SP-D polypeptides, each expressed SP-D polypeptide comprising a complex-type carbohydrate attached at an N-glycosylation site, wherein the population has a glycosylation pattern comprising the following characteristics: (i) at least 70% of the complex-type carbohydrates include a core fucose; (ii) at least 10% of the complex-type carbohydrates include at least one sialic acid residue; (iii) at least 50% of the complex-type carbohydrates include at least a biantennary carbohydrate structure; (iv) at least 10% of the complex-type carbohydrates include a bisecting N-acetylglucosamine; (v) less than 10% of the carbohydrates are high-mannose type structures; and (vi) a detectable amount of α2,6-coupled sialic acid residues.

In some embodiments, the population has a glycosylation pattern comprising one or more of the following characteristics: (i) at least 20% of the complex-type carbohydrates include a bisecting N-acetylglucosamine; and (ii) at least 85% of the complex-type carbohydrates include a core fucose.

In some embodiments, the polynucleotide encodes a dihydrofolate reductase polypeptide. In some embodiments, culturing the cell comprises contacting the cell with an antifolate. In some embodiments, expression of the SP-D polypeptide is increased by increasing the concentration of the antifolate. In some embodiments, the antifolate comprises methotrexate.

In some embodiments, the cell is cultured in a perfusion bioreactor.

In some embodiments, the cell is cultured in a continuous culture.

In some embodiments, culturing the cell comprises maintaining a growth medium having a pH 7.2, dissolved oxygen at 40% and or 20%, and temperature at 37° C. In some embodiments, the dissolved oxygen is lower than 35%, preferably 30%.

In some embodiments, isolating the expressed SP-D polypeptide from the cell comprises preparing a cell supernatant from a culture medium containing the cell.

Some embodiments of the methods and compositions provided herein include an expression vector encoding a leader polypeptide, a human surfactant protein D (SP-D) polypeptide, and a dihydrofolate reductase.

In some embodiments, the leader polypeptide is a wild type SP-D polypeptide leader sequence. In some embodiments, the leader polypeptide comprises SEQ ID NO:05.

In some embodiments, the polynucleotide encodes a polypeptide having an amino acid sequencing comprising SEQ ID NO:04.

In some embodiments, the leader polypeptide is a wild type T-cell receptor (TCR) polypeptide leader sequence. In some embodiments, the leader polypeptide comprises SEQ ID NO:10.

In some embodiments, the vector includes a polynucleotide having a sequence selected from the group consisting of SEQ ID NO:02 and 07.

In some embodiments, the vector includes encodes a polypeptide having an amino acid sequence selected from the group consisting of SEQ ID NO:04 and 09.

Some embodiments of the methods and compositions provided herein include an immortalized human cell comprising the expression vector of any one of the foregoing embodiments related to an expression vector. In some embodiments, the cell is derived from a human myeloid leukemia cell. In some embodiments, the cell is selected from the group consisting of NM-H9D8, NM-H9D8-E6Q12, and NM-F9. In some embodiments, the cell is a NM-H9D8 cell. In some embodiments, the cell is a NM-H9D8(8B11) cell.

Some embodiments of the methods and compositions provided herein include an immortalized human cell comprising an expression vector encoding a human surfactant protein D (SP-D) polypeptide, wherein the cell is derived from a human myeloid leukemia cell.

In some embodiments, the expression vector further encodes a leader polypeptide. In some embodiments, the leader polypeptide is a wild type SP-D polypeptide leader sequence. In some embodiments, the polypeptide comprises the amino acid sequence of SEQ ID NO:05. In some embodiments, the leader polypeptide is a wild type T-cell receptor (TCR) polypeptide leader sequence. In some embodiments, the leader polypeptide comprises the amino acid sequence of SEQ ID NO:10.

In some embodiments, the human surfactant protein D (SP-D) polypeptide comprises the amino acid sequence of positions 22 to 376 of SEQ ID NO:04.

In some embodiments, the expression vector further encodes a dihydrofolate reductase.

In some embodiments, the cell is selected from the group consisting of NM-H9D8, NM-H9D8-E6Q12, and NM-F9. In some embodiments, the cell is a NM-H9D8 cell. In some embodiments, the cell is a NM-H9D8(8B11) cell.

DETAILED DESCRIPTION

Figure 1:
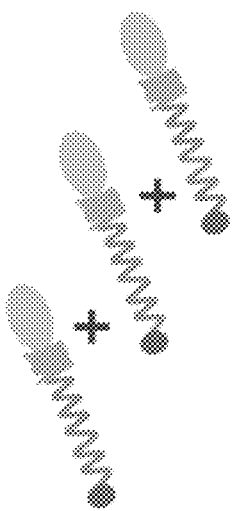
FIG. 1 is a schematic which depicts the formation of an SP-D trimer, and structural features of the SP-D trimer.
Figure 1:
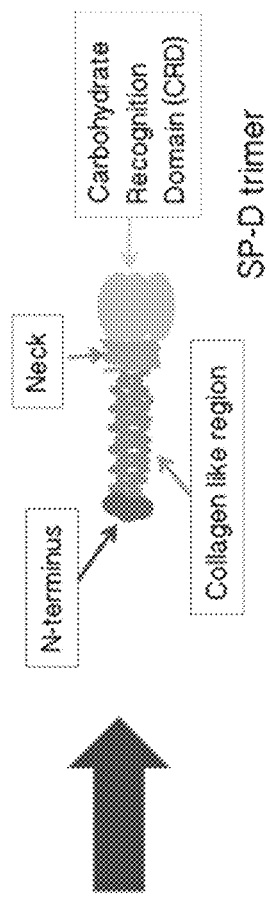

Surfactant protein D (SP-D) is a C-type ($Ca^{2+}$-dependent) lectin that comprises four domains: a cysteine-linked N-terminal region required for the formation of intermolecular disulfide bonds, a triple-helical collagen region, an α-helical-coiled-coil trimerizing neck peptide, and a C-terminal calcium-dependent carbohydrate-recognition domain (CRD) (Crouch E. et al. (1994) J Biol Chem, 269:17311-9). Monomers form trimers through folding of the collagenous region into triple helices and the assembly of a coiled-coil bundle of α-helices in the neck region (FIG. 1). These trimers are stabilized by two disulfide bonds in the cysteine-rich N-terminal domain. The SP-D trimer has a total molecular weight of 129 kDa which comprises three identical 43-kDa polypeptide chains. SP-D trimers can form higher order oligomerization states which vary by size and conformation. Higher order oligomerization states may be important for SP-D function (Hakansson K, et al., Protein Sci (2000) 9:1607-17; Crouch E. Respir Res (2000) 1:93-108; Crouch E. et al. (2006) J Biol Chem, 281:18008-14). The association of SP-D trimers into higher order oligomerization states is sensitive to environmental factors and conditions during purification and storage. The pathway and type of interactions involved in the formation of large oligomers of SP-D have not been previously elucidated. Some embodiments of the methods and compositions provided herein relate to the preparation and purification of certain forms of SP-D oligomers.

Human SP-D produced in mammalian Chinese hamster ovary (CHO) cells has been characterized by atomic force microscopy (AFM) and electrophoresis. A solution of rhSP-D can include a diverse population of different SP-D oligomeric forms including: trimers, hexamers, dodecamers, and larger oligomeric species identified as "fuzzy balls" which comprise more than 4 trimers. It was demonstrated in some embodiments of the present invention that production of SP-D as described herein, especially using the vectors and/or host cells and/or purification methods described herein, results in a higher yield of SP-D protein and a higher amount of SP-D dodecamers and a lower amount of larger oligomeric species compared to production of SP-D in CHO cells. It was demonstrated in some embodiments of the present invention that production of SP-D as described herein, especially using the vectors and/or host cells and/or purification methods described herein, results in a higher yield of SP-D protein and a higher relative amount of SP-D dodecamers and a lower relative amount of larger oligomeric species compared to production of rhSP-D in CHO cells. For example, the yield could be increased by up to about 5-15 fold, the relative amount of SP-D dodecamers in the purified rhSP-D composition as measured by means of SEC HPLC could be enhanced by about 30% or more and the relative amount of larger oligomeric species could be reduced by about 30% or more. The purification of the cell culture supernatant via Q-Sepharose and Superdex 75 columns does not alter the ratio of dodecamers to larger oligomeric species (such as fuzzy balls). Therefore, the relative amounts of the dodecamers and larger oligomeric species in the purified SP-D composition represent those in the cell culture supernatant.

Certain Expression Vectors and Cells

In one aspect, an expression vector comprising a polynucleotide encoding a human SP-D polypeptide is provided. Some embodiments include the preparation of expression vectors comprising a polynucleotide encoding a human SP-D polypeptide. Polymorphisms in the human SP-D polypeptide can include: residue 11, ATG (Met) ->ACG (Thr); residue 25, AGT (Ser) ->AGC (Ser); residue 160, ACA (Thr) ->GCA (Ala); residue 270, TCT (Ser) ->ACT (Thr); and residue 286, GCT (Ala) ->GCC (Ala) in which the positions relate to a position in the mature SP-D polypeptide. In some embodiments, the SP-D polypeptide comprises a certain residue at a polymorphic position in which the residue selected from Met11/31, Thr160/180, Ser 270/290, and Ala 286/306 in which residue positions relate to a position in the mature SP-D polypeptide, and a position in the SP-D polypeptide with its leader polypeptide. In some embodiments, the SP-D polypeptide comprises Met11/31. In some embodiments, the SP-D polypeptide comprises Met11/31, Thr160/180, Ser 270/290, and Ala 286/306. Examples of such sequences are provided in TABLE 1. In some embodiments, the SP-D is encoded by a nucleic acid having at least about 80%, 90%, 95%, 99% and 100%, or any range between any of the foregoing numbers, identity with a polynucleotide selected from SEQ ID NO:02 and SEQ ID NO:07 over the entire length of the polynucleotide. In some embodiments, the SP-D polypeptide has at least about 80%, 90%, 95%, 99% and 100%, or any range between any of the foregoing numbers, homology with a polypeptide selected from SEQ ID NO:04 and SEQ ID NO:09 over the entire length of the polynucleotide. In some embodiments, the SP-D polypeptide comprises the amino acid sequence of positions 22 to 376 of SEQ ID NO:04 or an amino acid sequence which is at least 80%, at least 90%, at least 95% or at least 99% identical thereto over the entire length of the reference sequence.

In some embodiments, the expression vector encodes a leader polypeptide located 5' of the nucleotide sequence encoding the SP-D polypeptide. In some embodiments the leader sequence is a wild type T cell receptor (TCR) leader sequence or a wild type SP-D leader sequence. Examples of such sequences are provided in TABLE 1. In some embodiments, the leader polypeptide is encoded by a nucleic acid having at least about 80%, 90%, 95%, 99% and 100%, or any range between any of the foregoing numbers, identity with a polynucleotide selected from SEQ ID NO:03 and SEQ ID NO:08 over the entire length of the polynucleotide. In some embodiments, the leader polypeptide has at least about 80%, 90%, 95%, 99% and 100%, or any range between any of the foregoing numbers, homology with a polypeptide selected from SEQ ID NO:05 and SEQ ID NO:10 over the entire length of the polynucleotide.

In some embodiments, the expression vector includes a selection gene useful to select for mammalian cells having the selection gene. Examples of such genes include those that encode proteins such as dihydrofolate reductase which provides resistance against antifolate compounds, such as methotrexate.

In one aspect, a cell comprising one or more of expression vectors comprising a polynucleotide encoding a human SP-D polypeptide is provided. Some embodiments include cells comprising one or more of the expression vectors described herein. Examples of such cells include mammalian cells that can modify an expressed SP-D polypeptide with a glycosylation pattern that enhances the activity and/or stability of the expressed SP-D polypeptide. Such cells include immortalized human blood cells, such as cells derived from a human myeloid leukemia. Examples of such cells include NM-H9D8 (DSM ACC 2806); NM-H9D8-E6Q12 (DSM ACC 2856); and NM-F9 (DSM ACC 2606) which have been deposited under the stated ACC code with the "DSMZ-Deutsche Sammlung von Mikroorganismen and Zellkulturen GmbH" in Braunschweig (Germany). NM-F9 was deposited by Nemod Biotherapeutics GmbH & Co. KG, Robert-Rossle-Str. 10, 13125 Berlin (DE) on Aug. 14, 2003, NM-H9D8 was deposited by Glycotope GmbH, Robert-Rössle-Str. 10, 13125 Berlin (DE) on Sep. 15, 2006, and NM-H9D8-E6Q12 was deposited by Glycotope GmbH, Robert-Rössle-Str. 10, 13125 Berlin (DE) on Aug. 8, 2007. More examples of useful cells lines can be found in U.S. Pat. No. 9,051,356, which is incorporated herein by reference in its entirety. In some embodiments, the cell comprising one or more of expression vectors comprising a polynucleotide encoding a human SP-D polypeptide is a cell of the cell line NM-H9D8.

Certain Methods for Producing Human SP-D

In one aspect, a method of producing a human SP-D polypeptide composition is provided. Some embodiments include methods of producing a human SP-D polypeptide composition by (a) introducing a polynucleotide encoding a human SP-D polypeptide into a mammalian cell; (b) culturing the cell under conditions in which the SP-D polypeptide is expressed; and (c) isolating the expressed SP-D polypeptide from the cell. Methods to introduce a polynucleotide encoding the SP-D polypeptide into a mammalian cell are well known in the art and include electroporation, transfection using cationic lipids, calcium phosphate, DEAE-dextran, or infection by virus particles such as adenoviruses or retroviruses or a combination thereof. Some such methods include linearizing an expression vector provided herein, and transfecting the linearized vector into a cell. In some embodiments, the cell and/or expression vector as described herein are used in the method of producing a human SP-D polypeptide composition. In some embodiments, the SP-D polypeptide is secreted by the mammalian cell. In these embodiments, the expressed SP-D polypeptide may be isolated from cell culture medium used for culturing the cell. In some embodiments, isolating the expressed SP-D polypeptide is done as described herein.

In some embodiments, the cell is derived from a human myeloid leukemia cell, such as a NM-H9D8, NM-H9D8-E6Q12, and NM-F9 cell line.

Some embodiments include methods of selecting cells comprising an expression vector. Some such embodiments can include culturing a cell with an antifolate, such as methotrexate. Transfectants can be isolated by methods such as subcloning, and cells which express SP-D can be readily identified by methods well known in the art, such as immunological methods using antibodies against SP-D in combination with ELISA, Western blots, and dot-blots.

In some embodiments, transfected cells which express SP-D at increased concentrations can be selected for by increasing the concentration of an antifolate, such as methotrexate in a culture medium.

Some embodiments include culturing cells that express SP-D in a perfusion bioreactor. Some such embodiments can include culturing cells by continuous fermentation. In perfusion mode, fresh media can be continuously supplied, and cell-free supernatant can be taken from the bioreactor while cells are held back in the fermenter. Cells can be held back by applying different techniques. For example filtration, centrifugation or sedimentation can be used. Example methods can be found in U.S. Pat. No. 9,359,427, which is incorporated by reference herein in its entirety.

Certain Methods for Isolating SP-D from a Culture Medium

In one aspect, a method of isolating human SP-D polypeptides is provided. Some embodiments include isolating expressed SP-D polypeptides from a culture medium. In one embodiment, the isolation is by using chromatography. Examples of chromatographic methods include affinity chromatography using affinity materials such as, Protein A, Protein G, anti-SP-D antibodies, lectin chromatography, antibodies against a certain tag introduced into an SP-D polypeptide such as HIS-tag or myc-tag, or antigen, or by other chromatography media such as, ion exchange chromatography, hydrophobic interaction chromatography, mixed-mode chromatography or size exclusion chromatography.

In some embodiments, a cell supernatant is prepared from a culture medium comprising a SP-D expressing cell. The supernatant can be filter-sterilized. In some embodiments, a cell supernatant comprising a SP-D polypeptide can be applied to column and the resulting eluate can be applied to a second column. In some embodiments, the SP-D polypeptide is isolated using anion exchange chromatography followed by affinity chromatography. In some embodiments, a strong anion exchange chromatography matrix such as Q-Sepharose is used for anion exchange chromatography. In some embodiments, a gel filtration chromatography matrix such as Superdex 75 matrix is used for affinity chromatography. In some embodiments, the cell supernatant is applied to a Q-Sepharose column with an equilibration and running buffer comprising 20 mM TRIS, 50 mM NaCl, pH 7.4. The SP-D can be eluted from the column using an elution buffer comprising 20 mM Tris, 600 mM NaCl, pH 7.4. In some such embodiments, the Q-Sepharose column eluate comprises about 0.2 to about 0.8 mg/ml SP-D.

Some embodiments include applying the fraction of the Q-Sepharose column eluate comprising SP-D to a second column, such as Superdex75 column. In some embodiments, the Q-Sepharose column eluate is diluted with the same volume of a 20 mM Tris buffer pH 7.4 containing 10 mM $CaCl_2$ and applied to a Superdex75 column with an equilibration and running buffer comprising 20 mM Tris, 300 mM NaCl, 5 mM $CaCl_2$, pH 7.4. The SP-D can be eluted from the column using an elution buffer comprising 20 mM Tris, 10 mM EDTA 300 mM NaCl, pH 7.4. In some such embodiments, the eluate comprises about 0.5 to about 2 mg/mL SP-D. In some such embodiments, the eluate comprises SP-D having greater than about 90% purity. Some embodiments also include dialyzing the eluate into a 5 mM Histidine buffer containing 200 mM NaCl, 1 mM EDTA, pH 7.0 prior to storage and analysis.

Posttranslational Modification of SP-D

One embodiment includes human SP-D polypeptides having a specific pattern of posttranslational modifications. Some embodiments include a composition comprising human SP-D polypeptides which are glycosylated, in particular N-glycosylated. In some embodiments, the glycosylated human SP-D polypeptides carry a carbohydrate structure at an asparagine corresponding to Asn90 of SEQ ID NO: 4 or 9. Carbohydrate structures at an N-glycosylation site may comprise a core structure of two N-actelyglucosamine (GlcNAc) residues and three mannose residues, wherein the first GlcNAc is attached to the polypeptide backbone, the second GlcNAc is attached to the first GlcNAc, the first mannose is attached to the second GlcNAc, and the second and third mannose are each attached to the first mannose. Further monosaccharide units may be attached to this core structure. In some embodiments, at least 60%, especially at least 70%, at least 75%, at least 80%, at least 85% or in particular at least 90% of the carbohydrate structures at the N-glycosylation site of SP-D in the composition are complex-type carbohydrate structures. Complex-type carbohydrate structures comprise at least one further GlcNAc residue attached to the second or third mannose residue, but do not comprise any further mannose residues.

In some embodiments, the human SP-D polypeptides in the composition have a glycosylation pattern at the N-glycosylation site comprising one or more of the following characteristics:

(i) a relative amount of carbohydrate structures carrying core fucose of at least 70% of the total amount of complex-type carbohydrate structures attached to the N-glycosylation site of SP-D in the composition; and/or (ii) a relative amount of carbohydrate structures carrying at least one sialic acid residue of at least 10% of the total amount of complex-type carbohydrate structures attached to the N-glycosylation site of SP-D in the composition; and/or (iii) a relative amount of at least biantennary carbohydrate structures of at least 50% of the total amount of complex-type carbohydrate structures attached to the N-glycosylation site of SP-D in the composition.

In some embodiments, the relative amount of carbohydrate structures carrying core fucose is at least 75% or at least 80% of the total amount of complex-type carbohydrate structures attached to the N-glycosylation site of SP-D in the composition. A core fucose residue is attached to the first GlcNAc residue of the core structure. A "relative amount of carbohydrate structures" according to the invention refers to a specific percentage or percentage range of the carbohydrate structures attached to SP-D in a composition. In particular, the relative amount of carbohydrate structures refers to a specific percentage or percentage range of all carbohydrate structures attached to the SP-D polypeptide chains in a composition. In some embodiments, only the carbohydrate structures attached to the N-glycosylation site of SP-D are considered.

In some embodiments, the relative amount of carbohydrate structures carrying at least one sialic acid residue is at least 15%, at least 20% or at least 25% of the total amount of complex-type carbohydrate structures attached to the N-glycosylation site of SP-D in the composition. The relative amount of carbohydrate structures carrying at least one sialic acid residue may be in the range of from 10% to 80%, from 15% to 75% or from 20% to 70%. In some embodiments, the glycosylation pattern of the human SP-D polypeptides in the composition comprises a relative amount of carbohydrate structures carrying two sialic acid residues of at least 0.5%, for example at least 1% or at least 2%, of the total amount of complex-type carbohydrate structures attached to the N-glycosylation site of SP-D in the composition. The relative amount of carbohydrate structures carrying at least two sialic acid residues may be in the range of from 0.5% to 30%, from 1% to 20% or from 1.5% to 15%. The term "sialic acid" in particular refers to any N- or O-substituted derivatives of neuraminic acid. It may refer to both 5-N-acetylneuraminic acid and 5-N-glycolylneuraminic acid, but preferably only refers to 5-N-acetylneuraminic acid. The sialic acid, in particular the 5-N-acetylneuraminic acid preferably is attached to a carbohydrate chain via a 2,3- or 2,6-linkage. Preferably, in the glycosylation pattern of SP-D described herein both 2,3- as well as 2,6-coupled sialic acids are present.

In some embodiments, the relative amount of at least biantennary carbohydrate structures is at least 60% or at least 70% of the total amount of complex-type carbohydrate structures attached to the N-glycosylation site of SP-D in the composition. In some embodiments, the glycosylation pattern of the human SP-D polypeptides in the composition comprises a relative amount of at least triantennary carbohydrate structures of at least 2%, for example at least 3% or at least 4%, of the total amount of complex-type carbohydrate structures attached to the N-glycosylation site of SP-D in the composition. Antennae are branches or one or more monosaccharide units which are attached to the terminal (i.e. the second or third) mannose residues of the core structure. In complex-type carbohydrate structures, an antenna generally comprises a GlcNAc residue, which may further carry a galactose residue and optionally a sialic acid residue. A biantennary complex-type carbohydrate structure comprises two antennae, i.e. to each of the two terminal mannose residues of the core structure at least a GlcNAc residue is attached. In a triantennary complex-type carbohydrate structure, one terminal mannose carries two antennae and the other terminal mannose carries one antenna. In a tetraantennary complex-type carbohydrate structure, both terminal mannoses each carry two antennae. The term "at least biantennary" includes bi- tri- and tetraantennary carbohydrate structures, while the term "at least triantennary" includes tri- and tetraantennary carbohydrate structures.

The A-number in glycosylation is a reference number for the antennarity of the glycan structures in a glycosylation pattern. The A-number is calculated by multiplying the relative amount of a specific antennarity with its number of antennae and adding the obtained numbers for each antennarity. In particular, the relative amount of monoantennary glycans is multiplied by 1, the relative amount of biantennary glycans is multiplied by 2, the relative amount of triantennary glycans is multiplied by 3 and the relative amount of tetraantennary glycans is multiplied by 4. The sum of these numbers results in the A-number. In some embodiments, the human SP-D polypeptides in the composition have a glycosylation pattern at the N-glycosylation site having an A-number of at least 185, for example at least 190.

In some embodiments, the human SP-D polypeptides in the composition have a glycosylation pattern at the N-glycosylation site comprising one or more of the following characteristics:

(i) a relative amount of carbohydrate structures carrying bisecting N-acetylglucosamine (bisGlcNAc) of at least 2%, for example at least 5% or at least 8%, of the total amount of complex-type carbohydrate structures attached to the N-glycosylation site of SP-D in the composition; and/or (ii) a relative amount of carbohydrate structures carrying at least one galactose residue of at least 40%, for example at least 45% or at least 50%, of the total amount of complex-type carbohydrate structures attached to the N-glycosylation site of SP-D in the composition; and/or (iii) a relative amount of carbohydrate structures carrying at least two galactose residues of at least 15%, for example at least 20% or at least 25%, of the total amount of complex-type carbohydrate structures attached to the N-glycosylation site of SP-D in the composition; and/or (iv) a relative amount of carbohydrate structures carrying an N-acetylgalactose residue of 30% or less, for example 20% or less or 15% or less, of the total amount of complex-type carbohydrate structures attached to the N-glycosylation site of SP-D in the composition; and/or (v) a relative amount of hybrid-type carbohydrate structures of 30% or less, for example 25% or less or 20% or less, of the total amount of carbohydrate structures attached to the N-glycosylation site of SP-D in the composition; and/or (vi) a relative amount of high-mannose-type carbohydrate structures of 25% or less, for example 20% or less or 15% or less, of the total amount of carbohydrate structures attached to the N-glycosylation site of SP-D in the composition.

A bisecting N-acetylglucosymine or bisGlcNAc residue is a GlcNAc residue attached to the central (i.e. first) mannose residue of the core structure of the carbohydrate structure. In some embodiments, the relative amount of carbohydrate structures carrying bisGlcNAc is in the range of from 2% to 50%, for example from 5% to 40% or from 8% to 35% of the total amount of complex-type carbohydrate structures attached to the N-glycosylation site of SP-D in the composition. A "high-mannose-type carbohydrate structure" comprises only mannose residues attached to the terminal mannoses of the core structure. A "hybrid-type carbohydrate structure" comprises mannose residues attached to one terminal mannose of the core structure and an antenna as described for complex-type carbohydrate structures attached to the other terminal mannose of the core structure.

In some embodiments, a population of SP-D polypeptides having a complex-type carbohydrate attached at the N-glycosylation site of the SP-D, can have a glycosylation pattern comprising one or more of the following characteristics:

(i) at least 20% of the complex-type carbohydrates include a bisecting N-acetylglucosamine;

(ii) at least 25% of the complex-type carbohydrates include at least one sialic acid residue;

(iii) at least 85% of the complex-type carbohydrates include a biantennary carbohydrate structure;

(iv) at least 0.5% of the complex-type carbohydrates include at least one GalNAc;

(v) less than 2% of the complex-type carbohydrates include 3 galactoses; and (vi) less than 2% of the complex-type carbohydrates include a triantennary carbohydrate structure.

In some embodiments, a population of SP-D polypeptides having a complex-type carbohydrate attached at the N-glycosylation site of the SP-D can have a glycosylation pattern that includes any of the following characteristics. In some embodiments, at least 15%, 18%, 19%, 20%, 25%, 30%, 35%, 38%, 40%, 45%, or a percentage in a range between any of the foregoing percentages of the complex-type carbohydrates of the carbohydrate structures attached to the N-glycosylation site of the SP-D of the population include a bisecting N-acetylglucosamine. In some embodiments, at least 75%, 80%, 82%, 85%, 90%, 95%, or a percentage in a range between any of the foregoing percentages of the complex-type carbohydrates of the carbohydrate structures attached to the N-glycosylation site of the SP-D of the population include a biantennary carbohydrate structure. In some embodiments, at least 1%, 2%, 3%, 4%, 5%, 6%, 7%, 8%, 9%, 10%, 11%, 15%, or a percentage in a range between any of the foregoing percentages of the complex-type carbohydrates of the carbohydrate structures attached to the N-glycosylation site of the SP-D of the population include at least one GalNAc. In some embodiments, less than 15%, 10%, 5%, 4%, 3%, 2%, 1%, or a percentage in a range between any of the foregoing percentages of the complex-type carbohydrates of the carbohydrate structures attached to the N-glycosylation site of the SP-D of the population include 3 galactose residues. In some embodiments, less than 15%, 13%, 10%, 5%, 4%, 3%, 2%, 1%, or a percentage in a range between any of the foregoing percentages of the complex-type carbohydrates of the carbohydrate structures attached to the N-glycosylation site of the SP-D of the population include a triantennary carbohydrate structure.

In some embodiments, the human SP-D polypeptides in the composition have a glycosylation pattern at the N-glycosylation site comprising the following characteristics:

(i) a relative amount of carbohydrate structures carrying bisecting GlcNAc of at least 10% of the total amount of complex-type carbohydrate structures attached to the N-glycosylation site of SP-D in the composition;

(ii) a relative amount of high-mannose-type carbohydrate structures 10% or less, of the total amount of carbohydrate structures attached to the N-glycosylation site of SP-D in the composition; and (iii) a detectable amount of complex-type carbohydrate structures carrying an α2,6-coupled sialic acid residue.

In further embodiments, the human SP-D polypeptides in the composition have a glycosylation pattern at the N-glycosylation site comprising the following characteristics:

(i) a relative amount of carbohydrate structures carrying core fucose of at least 85% of the total amount of complex-type carbohydrate structures attached to the N-glycosylation site of SP-D in the composition;

(ii) a relative amount of carbohydrate structures carrying bisecting GlcNAc of at least 20% of the total amount of complex-type carbohydrate structures attached to the N-glycosylation site of SP-D in the composition;

(iii) a relative amount of high-mannose-type carbohydrate structures 10% or less, of the total amount of carbohydrate structures attached to the N-glycosylation site of SP-D in the composition; and (iv) a detectable amount of complex-type carbohydrate structures carrying an α2,6-coupled sialic acid residue.

Identification of Oligomeric Species of SP-D

In one aspect, a method of identifying oligomeric species of human SP-D polypeptides is provided. Some embodiments include methods of identifying oligomeric species of SP-D, such as trimers, dodecamers, and oligomeric structures containing more than 4 trimers. Such methods can be useful to identify conditions and components for preparing formulations of SP-D having a certain amount of a certain oligomeric form, such as predominantly a dodecameric form. In some embodiments, methods for identifying oligomeric species of human SP-D polypeptides can include performing an asymmetric flow field-flow fractionation with multi-angle light scattering (AF4-MALS) analysis on a sample of SP-D. In some embodiments, methods can include performing a size exclusion chromatograph HPLC (SEC HPLC) for identifying oligomeric species of human SP-D polypeptides. Example conditions for SEC HPLC include: UHPLC: Dionex UltiMate 3000; column: TSKgel G6000PWXL, phase hydroxylated methacrylate, L×I.D. 30 cm×7.8 mm, 13 µm particle size (#0008024,Tosoh); column oven temperature: 30° C.; sampler temperature: 4° C.; pressure upper limit: 31 bar; UV detection: 280 nm; eluent: TBS, 10 mM EDTA, pH 7,4 (from 10×TBS Roti-Stock #1060.1, Carl Roth, EDTA #8040.2, Carl Roth); flow: 0.25 mL/min; samples injection: 20 µg or 30 µL fix volume; integration limits: HOO 25.0-30.0 min, dodecamer 30.0-34.5 min, LOO 34.5-44.0 min.

In some embodiments, methods of identifying oligomeric species of SP-D can include performing atomic force microscopy (AFM) on a sample of SP-D, identifying, and/or quantifying oligomeric species of SP-D in the AFM images. In some such embodiments, methods can include resolving a mixture of oligomeric species of SP-D by size. Some such methods include contacting a sample of SP-D with an anionic detergent, such as of sodium dodecyl sulfate (SDS); contacting the sample with a crosslinking reagent, such as 1% glutardialdehyde (GA); and resolving by size the species of SP-D, such as by performing polyacrylamide gel electrophoresis (PAGE). In some embodiments, the sample of SP-D is contacted with the anionic detergent prior to contacting the sample with the crosslinking reagent. In other embodiments, the sample of SP-D is contacted with the crosslinking reagent prior to contacting the sample with the anionic detergent. In some embodiments, the sample is contacted with a solution of about 1% GA. In some embodiments, the sample is contacted with a crosslinking reagent for a period between about 1 minute to about 30 minutes. In some embodiments, the PAGE is in the presence of sodium dodecyl sulfate (PAGE-SDS). In other embodiments, the PAGE is native PAGE. In some embodiments, the PAGE comprises a gradient gel. In some embodiments, the gradient gel is a 4-15% polyacrylamide gradient tris-glycine gel. In some embodiments, the PAGE is performed in the absence of a reducing agent. In some embodiments, the reducing agent comprises β-mercaptoethanol. Some embodiments also include identifying the species of SP-D, such as performing a Western blot.

Certain Compositions Comprising SP-D

Some embodiments include solutions comprising a population of rhSP-D polypeptides having a certain distribution of oligomeric forms of the SP-D. In some embodiments, the solution can include oligomeric forms of the SP-D in which greater than about 30%, 40%, 50%, 60%, 61%, 62%, 63%, 64%, 65%, 70%, or any range between the foregoing numbers, of the oligomeric forms comprise dodecamers of the SP-D. In some embodiments, a distribution of the oligomeric forms of the SP-D can be measured by methods provided herein, such as an asymmetric flow field-flow fractionation with multi-angle light scattering (AF4-MALS) analysis. In some embodiments, the solution of rhSP-D polypeptides is prepared by a method provided herein. In some embodiments, the method of producing a human SP-D polypeptide composition as described herein produces a solution comprising a population of rhSP-D polypeptides as described herein. In some embodiments, the method of isolating human SP-D polypeptides as described herein produces a solution comprising a population of rhSP-D polypeptides as described herein. In some embodiments of the method of producing a human SP-D polypeptide composition as described herein, the expressed SP-D polypeptide is predominantly in dodecameric form. In some embodiments of the method of isolating human SP-D polypeptides as described herein, the isolated SP-D polypeptide is predominantly in dodecameric form. "Predominantly" in this respect may in particular refer to a relative amount of at least 30% of all SP-D polypeptides in the composition, such as at least 40%, at least 45%, at least 50% or at least 55% of all SP-D polypeptides in the composition. In some embodiments, "predominantly" refers to a relative amount of more than 50% of all SP-D polypeptides in the composition.

EXAMPLES

Example 1

Construction of SP-D Expression Vectors

Two expression vectors were developed for expression of human SP-D in human mammalian cells. One vector included a wild-type human SP-D leader/signal sequence; the other vector included a human T-cell receptor (TCR) leader/signal sequence. The TCR leader sequence was selected for one of the expression vectors because the proteins would be expressed in human myeloid leukemia cells which would be expected to secrete proteins with a TCR leader sequence at a high efficiency.

Figure 2A:
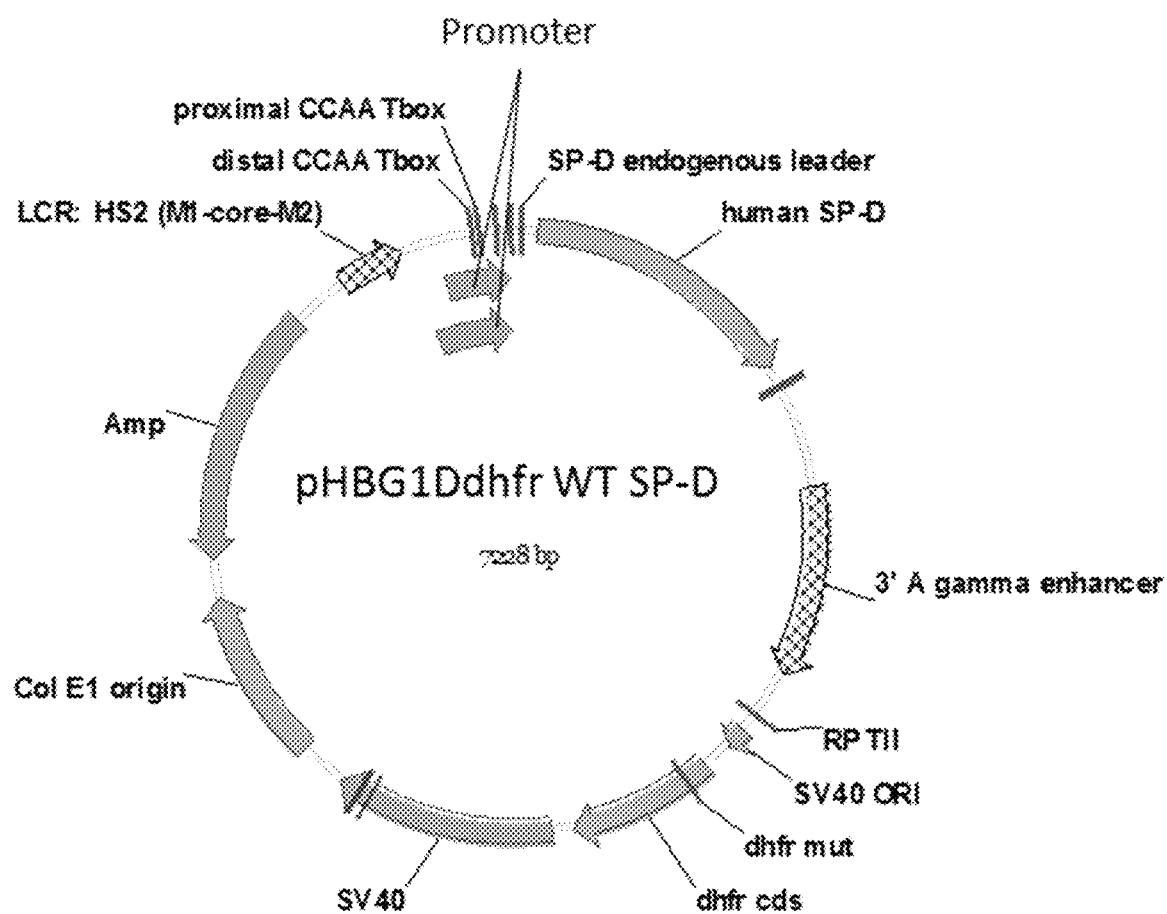
FIG. 2A is a map of the expression vector pHBG1Ddhfr_WT_SP-D (7228 bp) which contains a polynucleotide encoding a human SP-D, a human SP-D leader sequence, and dihydrofolate reductase (DHFR).
Figure 2B:
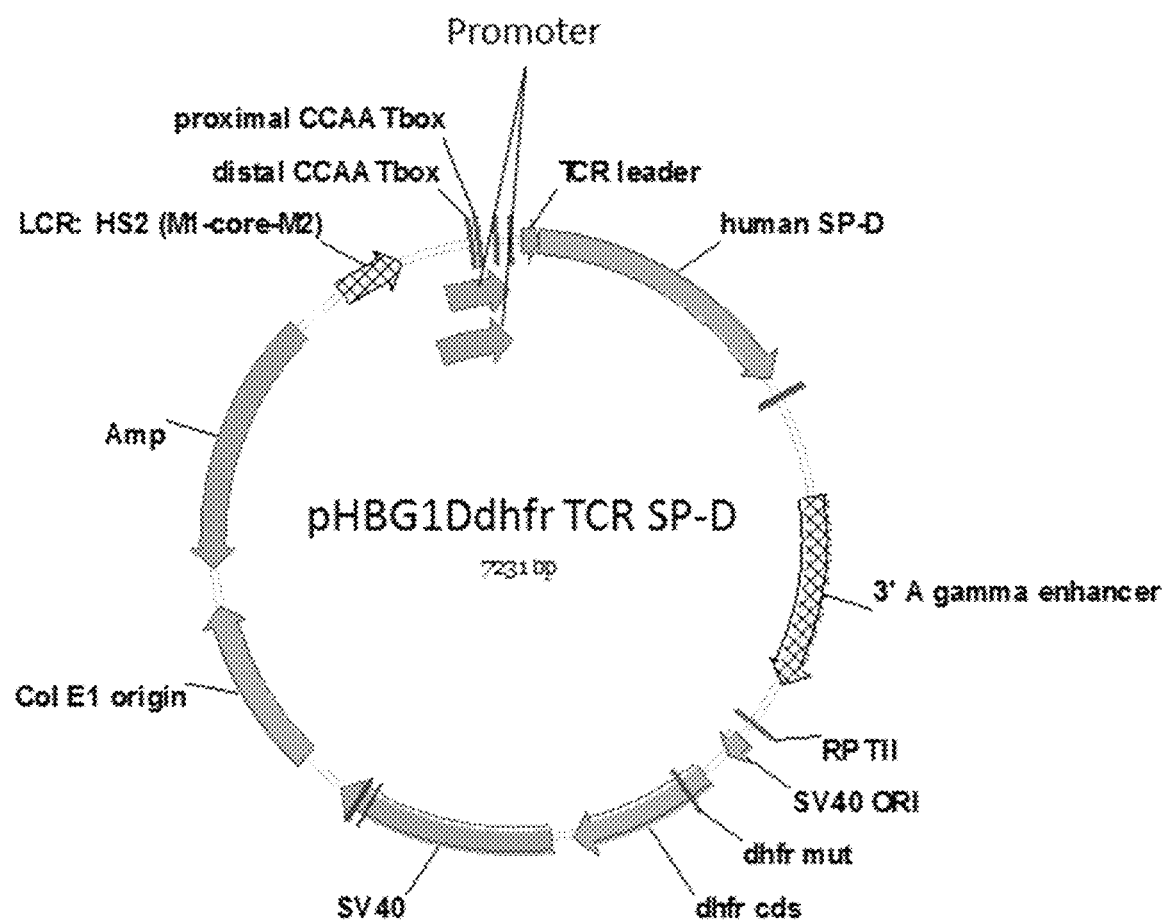
FIG. 2B is a map of the expression vector pHBG1Ddhfr_TCR_SP-D (7231 bp) which contains a polynucleotide encoding a human SP-D, a human T-cell receptor (TCR) leader sequence, and dihydrofolate reductase (DHFR).
Figure 2C:
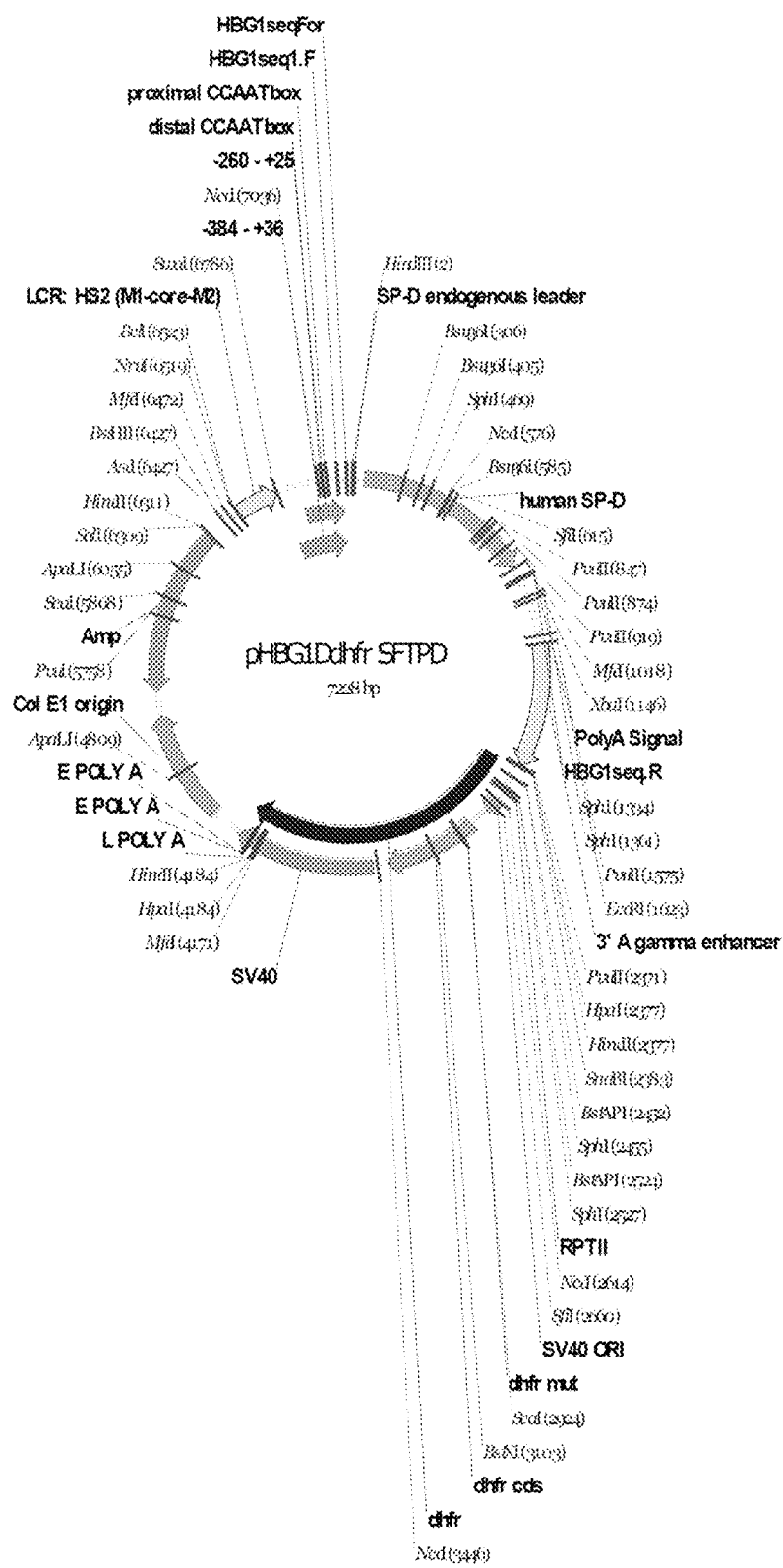
FIG. 2C is a is a map of the expression vector pHBG1Ddhfr_SFTPD (7228 bp) which contains a polynucleotide encoding a human SP-D, a human SP-D leader sequence, and dihydrofolate reductase (DHFR).

Polynucleotides encoding a human SP-D polypeptide and including either the wild-type human SP-D leader/signal sequence or the human T-cell receptor (TCR) leader/signal sequence were synthesized by GENEART (ThermoFisher Scientific). Each polynucleotide included Xba I (5' end) and Hind III (3' end) restriction sites for cloning purposes, and a Kozak consensus sequence. Each polynucleotide was excised from a GENEART (ThermoFisher Scientific) delivery vector by Hind III/Xba I restriction, and ligated into a cloning vector pHBG1Ddhfr (Glycotope GmbH, Germany) to obtain the expression vectors: pHBG1Ddhfr_WT_SP-D (7228 bp), and pHBG1Ddhfr_TCR_SP-D (7231 bp). See FIG. 2A and FIG. 2B. An additional example expression vector is shown in FIG. 2C. The expression vectors were sequenced, and restriction mapped to confirm the correct sequence. TABLE 1 lists certain sequences.

TABLE 1

| SEQ ID NO. | Sequence |
|---|---|
| SEQ ID NO: 01<br>Polynucleotide encoding a SP-D polypeptide with an endogenous SP-D leader sequence, kozak sequence (underlined), and Xba I (5' end) and Hind III (3' end) restriction sites. | aagctt<u>gccacc</u>atgctgctgtttctgctgagcgccctggtgctgctgacacagcctctgggc<br>tatctggaagccgagatgaagacctacagccaccggaccatgcccagcgcctgtaccctcg<br>tgatgtgcagcagcgtggaaagcggcctgcctggcagagatggcagggatggaagagag<br>ggccccagaggcgagaagggcgatcctggactgcctggcgctgcagggcaggctggaat<br>gcctggacaggctggacctgtgggccccaagggcgataatggctctgtgggagagcctgg<br>ccctaaggggatacaggccatctggacctcctggaccacctggcgtgccaggacctgct<br>ggaagagaaggacctctgggcaagcagggcaacatcggccctcagggaaagccaggac<br>caaagggcgaggccggacccaaaggcgaagtgggagcacctggcatgcagggaagtgc<br>cggcgctagaggactggctggcccaaaaggcgaaaggggagtgcctggcgaaagaggc<br>gtgcccggaaatactggcgccgctggatctgctggcgccatgggacctcagggatctccag<br>gcgcaagaggccctccaggcctgaaaggcgacaaaggcatccccggcgataagggcgc<br>taagggcgaatccggcctgccagatgtggccagcctgagacagcaggtggaagctctcca<br>gggccaggtgcagcatctccaggctgccttcagccagtacaagaaggtggaactgttcccc<br>aacggccagagcgtgggcgagaagatctttaagaccgccggatcgtgaagccatcacc<br>gaggctcagctgctgtgtacccaggctggcggacagctggcctctcctagatctgccgccg<br>aaaatgccgctctccagcagctggtggtggccaagaatgaggccgccttcctgagcatgac<br>cgacagcaagaccgagggcaagttcacctaccccaccggcgagtccctggtgtacagcaa<br>ttgggcccctggcgagcccaacgatgatggcggctctgaggactgcgtggaaatcttcacc<br>aacggcaagtggaacgaccgggcctgtggcgagaaaagactggtcgtgtgcgagttctga<br>agggtctaga |
| SEQ ID NO: 02<br>Polynucleotide encoding a SP-D polypeptide with an endogenous SP-D leader sequence. | gccaccatgctgctgtttctgctgagcgccctggtgctgctgacacagcctctgggctatctg<br>gaagccgagatgaagacctacagccaccggaccatgcccagcgcctgtaccctcgtgatg<br>tgcagcagcgtggaaagcggcctgcctggcagagatggcagggatggaagagagggcc<br>ccagaggcgagaagggcgatcctggactgcctggcgctgcagggcaggctggaatgcct<br>ggacaggctggacctgtgggccccaagggcgataatggctctgtgggagagcctggccct<br>aaggggatacaggccatctggacctcctggaccacctggcgtgccaggacctgctgga<br>agagaaggacctctgggcaagcagggcaacatcggccctcagggaaagccaggacaa<br>agggcgaggccggacccaaaggcgaagtgggagcacctggcatgcagggaagtgccg<br>gcgctagaggactggctggcccaaaaggcgaaaggggagtgcctggcgaaagaggcgt<br>gcccggaaatactggcgccgctggatctgctggcgccatgggacctcagggatctccagg<br>cgcaagaggccctccaggcctgaaaggcgacaaaggcatccccggcgataagggcgcta<br>agggcgaatccggcctgccagatgtggccagcctgagacagcaggtggaagctctccag<br>ggccaggtgcagcatctccaggctgccttcagccagtacaagaaggtggaactgttcccca<br>acggccagagcgtgggcgagaagatctttaagaccgccggatcgtgaagccatcaccg<br>aggctcagctgctgtgtacccaggctggcggacagctggcctctcctagatctgccgccga<br>aaatgccgctctccagcagctggtggtggccaagaatgaggccgccttcctgagcatgacc<br>gacagcaagaccgagggcaagttcacctaccccaccggcgagtccctggtgtacagcaat<br>tgggcccctggcgagcccaacgatgatggcggctctgaggactgcgtggaaatcttcacca<br>acggcaagtggaacgaccgggcctgtggcgagaaaagactggtcgtgtgcgagttctgaa<br>ggg |
| SEQ ID NO: 03<br>The polynucleotide encoding the endogenous leader sequence in SEQ ID NO: 01. | atgctgctgtttctgctgagcgccctggtgctgctgacacagcctctgggctatctggaa |
| SEQ ID NO: 04<br>SP-D polypeptide encoded by SEQ ID NO: 01 including a leader sequence (underlined) and polymorphisms (underlined) at: Met11/31, Thr160/180, Ser 270/290, Ala 286/306. | <u>MLLFLLSALVLLTQPLLGYLE</u>AEMKTYSHRT<u>M</u>PSACTLV<br>MCSSVESGLPGRDGRDGREGPRGEKGDPGLPGAAGGQAG<br>MPGQAGPVGPKGDNGSVGEPGPKGDTGPSGPPGPPGVPG<br>PAGREGPLGKQGNIGPQGKPGPKGEAGPKGEVGAPGMQG<br>SAGARGLAGPKGERGVPGERGVPGN<u>T</u>GAAGSAGAMGPQ<br>GSPGARGPPGLKGDKGIPGDKGAKGESGLPDVASLRQQV<br>EALQGGQVQHLQAAFSQYKKVELFPNGQSVGEKIFKTAGF<br>VKPFTEAQLLCTQAGGQLA<u>S</u>PRSAAENAALQQLVV<u>A</u>KNE<br>AAFLSMTDSKTEGKFTYPTGESLVYSNWAPGEPNDDGGS<br>EDCVEIFTNGKWNDRACGEKRLVVCEF |
| SEQ ID NO: 05<br>The leader sequence in SEQ ID NO: 04. | MLLFLLSALVLLTQPLLGYLE |
| SEQ ID NO: 06<br>Polynucleotide encoding a SP-D polypeptide with a TCR leader sequence, kozak sequence (underlined), and Xba I (5' end) and Hind III (3' end) restriction sites. | aagctt<u>gccacc</u>atggcctgccccggatttctgtgggccctcgtgatcagcacctgtctggaa<br>ttcagcatggccgccgagatgaagacctacagccaccggacaatgcccagcgcctgcacc<br>ctcgtgatgtgcagctctgtggaaagcggcctgcccggcagagatggcagggatggaaga<br>gagggacccagaggcgagaagggcgatcctggactgcctggcgctgcagggcaggctg<br>gaatgcctggacaggctggacctgtgggccccaagggcgataatggctctgtgggagagc<br>ctggcctaaggggatacaggcccttctggacctcctggaccacctggcgtgccaggac<br>ctgctggaagagaaggacctctgggcaagcagggcaacatcggccctcagggaaagcca<br>ggaccaaagggcgaggccggacccaaaggcgaagtgggagcacctggcatgcagggaa<br>gtgccggcgctagaggactggctggcccaaaaggcgaaaggggagtgcctggcgaaa<br>gaggcgtgcccggaaatactggcgccgctggatctgctggcgccatgggacctcagggat<br>ctccaggcgcaagaggccctccaggcctgaaaggcgacaaaggcatccccggcgataag<br>ggcgctaagggcgaatccggcctgccagatgtggccagcctgagacagcaggtggaagc<br>tctccagggccaggtgcagcatctccaggctgccttcagccagtacaagaaggtggaactg |

TABLE 1-continued

| SEQ ID NO. | Sequence |
|---|---|
| | ttccccaacggccagagcgtgggcgagaagatctttaagaccgccggcttcgtgaagccct<br>tcaccgaggctcagctgctgtgtacccaggctggcggacagctggcctctcctagatctgcc<br>gccgaaaatgccgctctccagcagctggtggtggccaagaatgaggccgccttcctgagc<br>atgaccgacagcaagaccgagggcaagttcacctacccaccggcgagtccctggtgtac<br>agcaattgggcccctggcgagcccaacgatgatggcggctctgaggactgcgtggaaatct<br>tcaccaacggcaagtggaacgacccgggcctgtggcgagaaaagactggtcgtgtgcgagt<br>tctgaagggtctaga |
| SEQ ID NO: 07<br>Polynucleotide encoding<br>a SP-D polypeptide with<br>a TCR leader sequence. | gccaccatggcctgccccggatttctgtgggccctcgtgatcagcacctgtctggaattcagc<br>atggccgccgagatgaagacctacagccaccggacaatgcccagcgcctgcaccctcgtg<br>atgtgcagctctgtggaaagcggcctgcccggcagagatggcagggatggaagagaggg<br>acccagaggcgagaagggcgatcctggactgcctggcgctgcagggcaggctggaatgc<br>ctggacaggctggacctgtgggcccaagggcgataatggctctgtgggagagcctggcc<br>ctaaggggatacaggccttctggacctcctggaccacctggcgtgccaggacctgctgg<br>aagagaaggacctctgggcaagcagggcaacatcggccctcagggaaagccaggacca<br>aagggcgaggccggacccaaaggcgaagtgggagcacctggcatgcagggaagtgcc<br>ggcgctagaggactggctggcccaaaaggcgaaaggggagtgcctggcgaaagaggcg<br>tgcccggaaatactggcgccgctggatctgctggcgccatgggacctcagggatctccagg<br>cgcaagaggccctccaggcctgaaaggcgacaaaggcatccccggcgataaggggcgcta<br>agggcgaatccggcctgccagatgtggccagcctgagacagcaggtggaagctctccag<br>ggccaggtgcagcatctccaggctgccttcagccagtacaagaaggtggaactgttcccca<br>acggccagagcgtgggcgagaagatctttaagaccgccggcttcgtgaagcccttcaccg<br>aggctcagctgctgtgtaccaggctggcggacagctggcctctcctagatctgccgccga<br>aaatgccgctctccagcagctggtggtggccaagaatgaggccgccttcctgagcatgacc<br>gacagcaagaccgagggcaagttcacctacccaccggcgagtccctggtgtacagcaat<br>tgggcccctggcgagcccaacgatgatggcggctctgaggactgcgtggaaatcttcacca<br>acggcaagtggaacgacccgggcctgtggcgagaaaagactggtcgtgtgcgagttctgaa<br>ggg |
| SEQ ID NO: 08<br>The polynucleotide<br>encoding the leader<br>sequence in SEQ ID<br>NO: 06. | atggcctgccccggatttctgtgggccctcgtgatcagcacctgtctggaattcagcatggcc |
| SEQ ID NO: 09<br>SP-D polypeptide<br>encoded by SEQ ID<br>NO: 06 including a TCR<br>leader sequence<br>(underlined) and<br>polymorphisms<br>(underlined) at:<br>Met11/31, Thr160/180,<br>Ser 270/290, Ala<br>286/306. | <u>MACPGFLWALVISTCLEFSMA</u>AEMKTYSHRT<u>M</u>PSACTLV<br>MCSSVESGLPGRDGRDGREGPRGEKGDPGLPGAAGQAG<br>MPGQAGPVGPKGDNGSVGEPGPKGDTGPSGPPGPPGVPG<br>PAGREGPLGKQGNIGPQGKPGPKGEAGPKGEVGAPGMQG<br>SAGARGLAGPKGERGVPGERGVPGN<u>T</u>GAAGSAGAMGPQ<br>GSPGARGPPGLKGDKGIPGDKGAKGESGLPDVASLRQQV<br>EALQGQVQHLQAAFSQYKKVELFPNGQSVGEKIFKTAGF<br>VKPFTEAQLLCTQAGGQLA<u>S</u>PRSAAENAALQQLVV<u>A</u>KNE<br>AAFLSMTDSKTEGKFTYPTGESLVYSNWAPGEPNDDGGS<br>EDCVEIFTNGKWNDRACGEKRLVVCEF |
| SEQ ID NO: 10<br>The leader sequence in<br>SEQ ID NO: 09. | MACPGFLWALVISTCLEFSMA |

Example 2

Expression of SP-D in Mammalian Cell Lines

Prior to transfection, expression vectors were linearized with Pvu I and purified with phenol/chloroform, and trichlormethan/chloroform. Cell lines were transfected with 7-8 μg of a linearized expression vector using NUCLEOFECTION according to the manufacturer's instructions (AMAXA NUCLEOFECTOR TECHNOLOGY; Lonza, Cologne, Germany). The following cell lines were transfected with expression vectors: NM-H9D8 (DSM ACC 2806); NM-H9D8-E6Q12 (DSM ACC 2856); and NM-F9 (DSM ACC2606).

Pools of cells expressing SP-D were selected using 25 nM methotrexate (MTX) and increasing the concentration to 50 nM MTX. To obtain cells with increasing levels of SP-D expression, the concentration of MTX was increased in steps from 100 nM to 200 nM to 400 nM MTX. The productivity of SP-D producing cells was determined by SP-D specific ELISA (BioVendor GmbH, Germany, Cat# RD194059101) according to the manufacturer's instructions, and/or Dot-Blot analysis using SP-D specific antibodies (Seven Hills Bioreagents, Cincinnati Ohio, Cat# WMAB-2D12A88 and Cat# WMAB-1A10A9). The specific production rate (SPR) was calculated using the following equations:

$$SPR = \frac{\text{total protein mass}}{\text{integral cell area } (ICA)}$$

$$ICA = \frac{(\text{final cell number} - \text{initial cell number}) \times \text{days in culture}}{\log_e(\text{final cell number}/\text{initial cell number})}$$

Doubling time was calculated by following equation:

$$g = \log 2 \times (\text{hours in culture})/\log (\text{final cell number}/\text{initial cell number})$$

Figure 3:
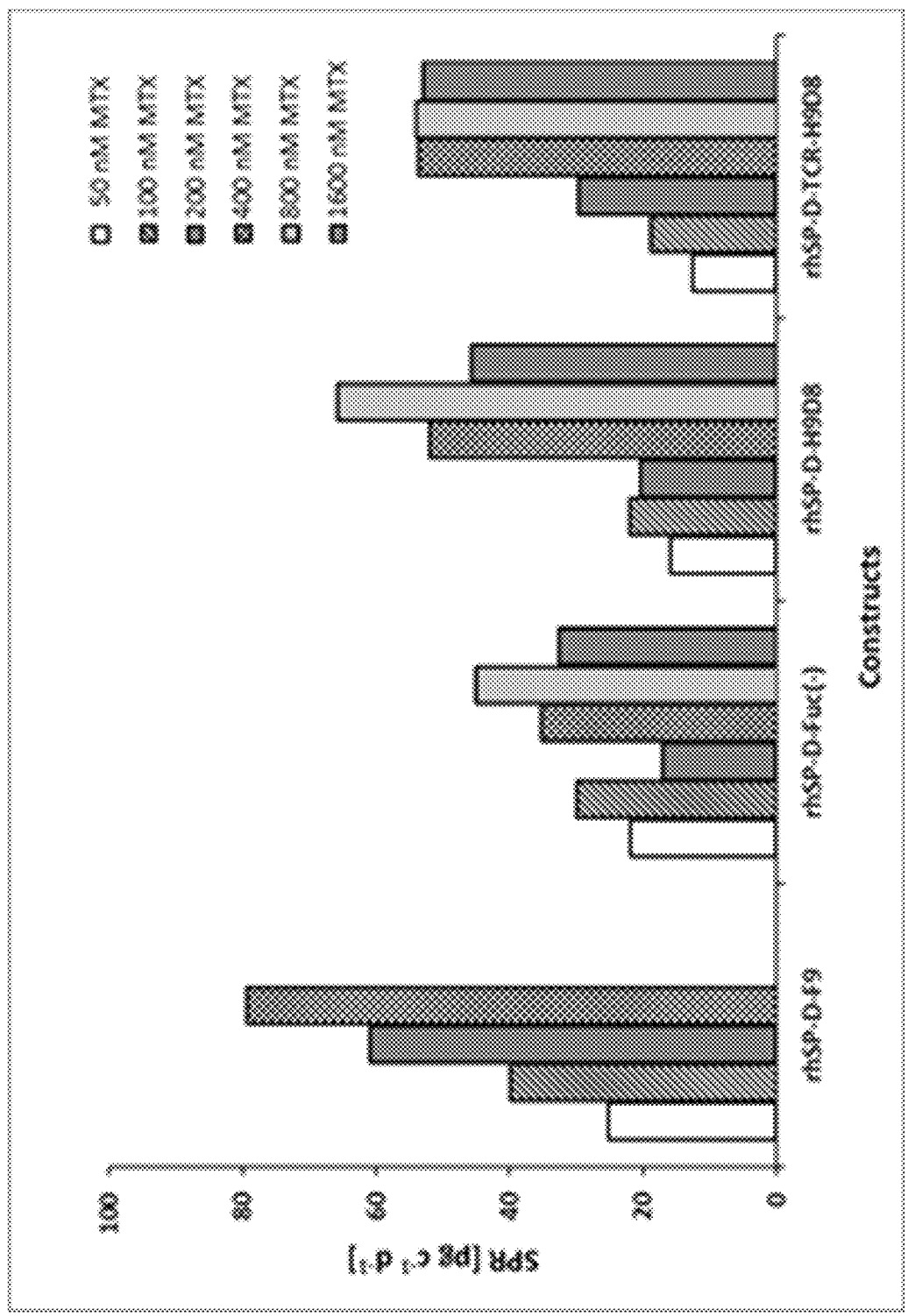
FIG. 3 is a bar graph showing specific production rates for pools cultured with various methotrexate (MTX) concentrations. Cell line pools included 'rhSP-D-F9', 'rhSP-D-Fuc(−)', 'rhSP-D-H9D8' which were F9 cells, H9D8-E6Q12 cells, and H9D8 cells each transfected with the human SP-D expression vector containing the human SP-D leader sequence, respectively; and 'rhSP-D-TCR-H9D8' which was H9D8 cells transfected with the human SP-D expression vector containing the human TCR leader sequence.

SP-D expressing clones were isolated from cell pools by means of the ClonePix (Molecular Devices) technology and assessed for productivity. Selected clones were further subcloned to obtain final clones. Clones with a productivity >100 picogram/cell/day (pcd) were obtained. FIG. 3 shows specific production rates for different SP-D producing cell pools cultured with various MTX concentrations. Cell pools included H9D8-E6Q12 cells, H9D8 cells and F9 cells each transfected with the human SP-D expression vector containing the human SP-D leader sequence, and H9D8 cells transfected with the human SP-D expression vector containing the human TCR leader sequence.

Example 3

Culturing SP-D Expressing Cell Lines

Cells were cultured in a serum-free chemically defined gene therapy medium (GTM) (Glycotope GmbH, Germany). See e.g., U.S. Pat. No. 9,359,427 which is incorporated by reference in its entirety for a description of the GTM culture media. Perfusion process cultures were initiated with 1×GTM, and then modified to 2×GTM. Cells were maintained in exponential growth phase by splitting every 2 to 3 days to a cell concentration of $1\times10^5$ to $3\times10^5$ cells/mL in T flasks (25 cm², 3 to 6 mL suspension volume, TPP, Germany) and were incubated at 37° C., 98% humidity and 8% $CO_2$ (Integra Biosciences IBS, Biosafe plus, Switzerland or Thermo/Heraeus BBD 6220, Germany). Cell expansion was carried out using T flasks (75 cm², 12 to 30 mL Volume; 150 cm², 50 to 150 mL) and Spinner flasks (100 mL to 1000 mL, Integra Biosciences IBS, Cellspin, Switzerland).

General cultivation parameters: media were inoculated with $2.0\times10^5$ cells/mL. Continuous operation was enabled by feeding 1×GTM at a perfusion rate of 0.5 V/d (usually day 4-5) and, depending on cell growth and nutrient requirements, increased to a maximum perfusion rate of two reactor volumes per day. When maximum perfusion with 1×GTM was achieved, feed medium was replaced by modified 2×GTM. Media was maintained at pH 7.2 by either addition of 0.5 M NaOH or sparging with $CO_2$. Dissolved oxygen was set to 40% and a temperature to 37° C. Lowering the dissolved oxygen below 40% to e.g. to 20% dissolved oxygen is as well possible. In the latter case the content of docdecamer can be slightly increased compared to culturing under 40% dissolved oxygen.

1 L perfusion bioreactor: Laboratory 1 L scale cultivations were carried out in Sartorius Biostat B-DCU 2l Quad system or 2L BBI Quad system. Dissolved oxygen and pH were measured by standard electrodes (Mettler Torledo InPro 6800 and Mettler-Torledo 405-DPAS-SC-K8S, respectively, Mettler Torledo, Switzerland). Agitation was performed by 3-blade segment impellers with a stirring rate of 300 to 400 rpm. Perfusion was performed using an ATF2 module with a 60 cm PES membrane (0.2 µm pore size and 0.15 m² membrane area, Spectrum, USA) and a flow rate of 0.9 L/min. In Process control: Cell concentration and viability were determined by Cedex HiRes (Roche, Switzerland) using the trypan blue exclusion principle. Glucose/lactate and glutamine/glutamate were measured by YSI2700 or YSI2900 Select Biochemical Analyzer (Yellow Springs Instruments, USA).

Figure 4:
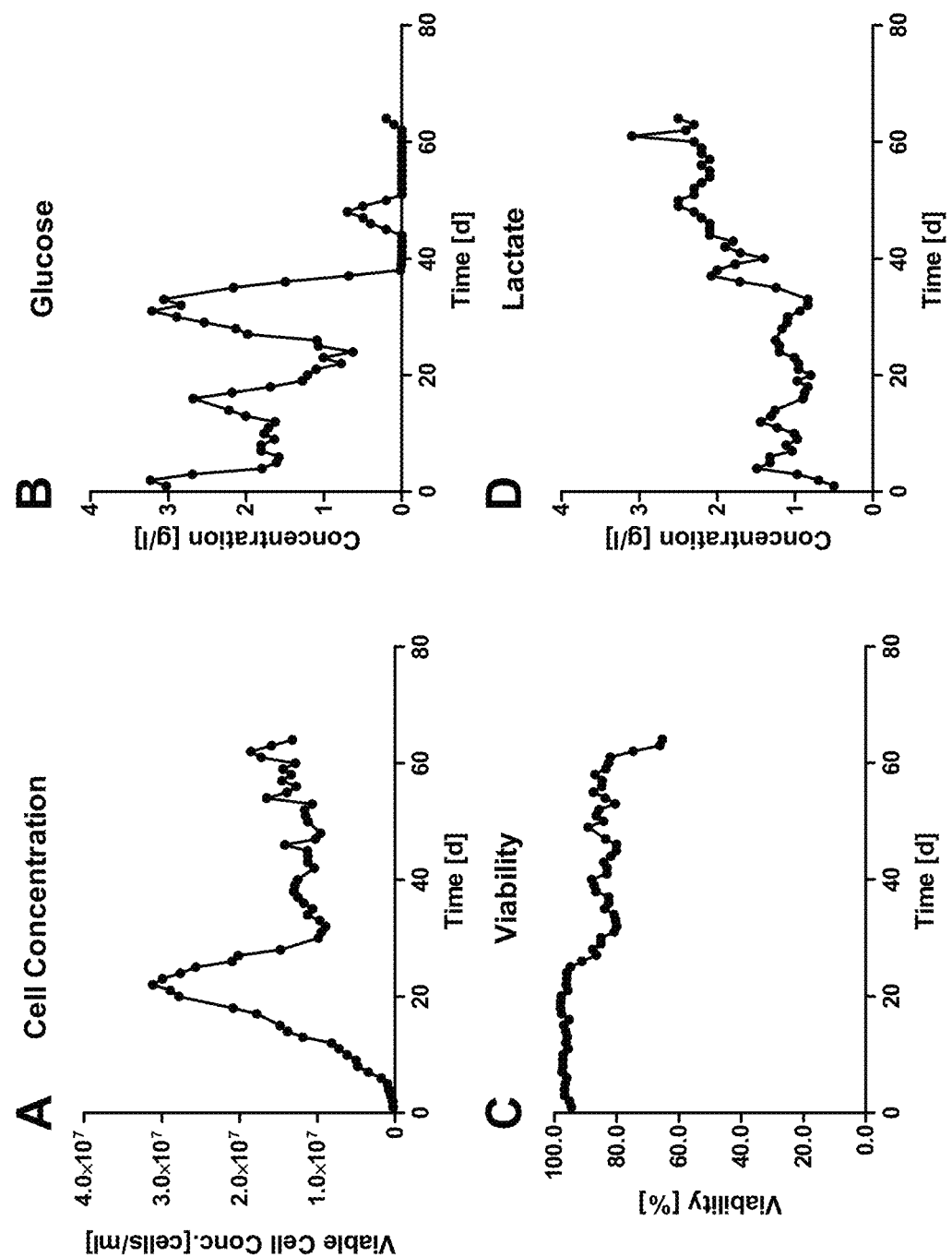
FIG. 4 is a series of graphs showing changes in culture conditions over time from a bioreactor run for clone H9D8-P1315-2A5 including: viable cell concentration (panel A); glucose concentration (panel B); cell viability (panel C); lactate concentration (panel D).

FIG. 4 shows changes in culture conditions over time from a bioreactor run for clone H9D8-P1315-2A5 including: viable cell concentration (panel A); glucose concentration (panel B); cell viability (panel C); lactate concentration (panel D).

Example 4

Purification of SP-D from Mammalian Cell Lines

SP-D was found be secreted from expressing cells. Cell supernatant from SP-D producing cells was collected from the bioreactor runs or other cultures and purified using Q-Sepharose chromatography run (Q-Sepharose FF; GE Healthcare) in bind and elute mode, followed by a Superdex75 chromatography run (Superdex75; GE Healthcare) performed in bind and elute mode. The chromatography was performed on FPLC systems from GE (Äkta Explorer, Äkta Avant, Äkta Pure).

Q-Sepharose chromatography: the supernatant was sterile filtered and diluted with the same volume of a solution of 20 mM TRIS, 10 mM EDTA, pH 7.4 and loaded on the Q-Sepharose column and eluted by step elution with 600 mM NaCl. The chromatography was performed with the settings shown in TABLE 2.

TABLE 2

| Parameter | Setting |
| --- | --- |
| Equilibration and running buffer | 20 mM TRIS, 50 mM NaCl, pH 7.4 |
| Elution buffer | 20 mM Tris, 600 mM NaCl, pH 7.4 |
| Column volume/length | 240 mL/11.5 cm 24000 mL |
| Load per mL Col. Vol. | 100 mL |
| Total load | 24000 ml (1:2 dilution) |
| Flow rate (ml/min) | 55 mL/min |
| Dynamic flow rate (cm/min) | 2.6 cm/min |
| Contact time | 4.4 min |
| SP-D concentration in eluate | 0.2-2 mg/ml |

Superdex75 chromatography: the eluate was diluted with the same volume of a 20 mM Tris buffer pH 7.4 containing 10 mM $CaCl_2$ and loaded onto the Superdex75 column and eluted by step elution with 10 mM EDTA. The chromatography was performed with the settings shown in TABLE 3.

TABLE 3

| Parameter | Setting |
| --- | --- |
| Equilibration and running buffer | 20 mM Tris, 300 mM NaCl, 5 mM $CaCl_2$, pH 7.4 |
| Elution buffer | 20 mM Tris, 10 mM EDTA 300 mM NaCl, pH 7.4 |
| Total load | 2228 mL |
| Column volume/length | 106 mL/21.5 cm |
| Load per mL Col. Vol. | 21 mL (1:2 dilution) |
| Flow rate (ml/min) | 5 mL/min |
| Dynamic flow rate (cm/min) | 1.01 cm/min |
| Contact time | 21.2 min |
| Elution concentration | 0.5-3 mg/mL |

Figure 5:
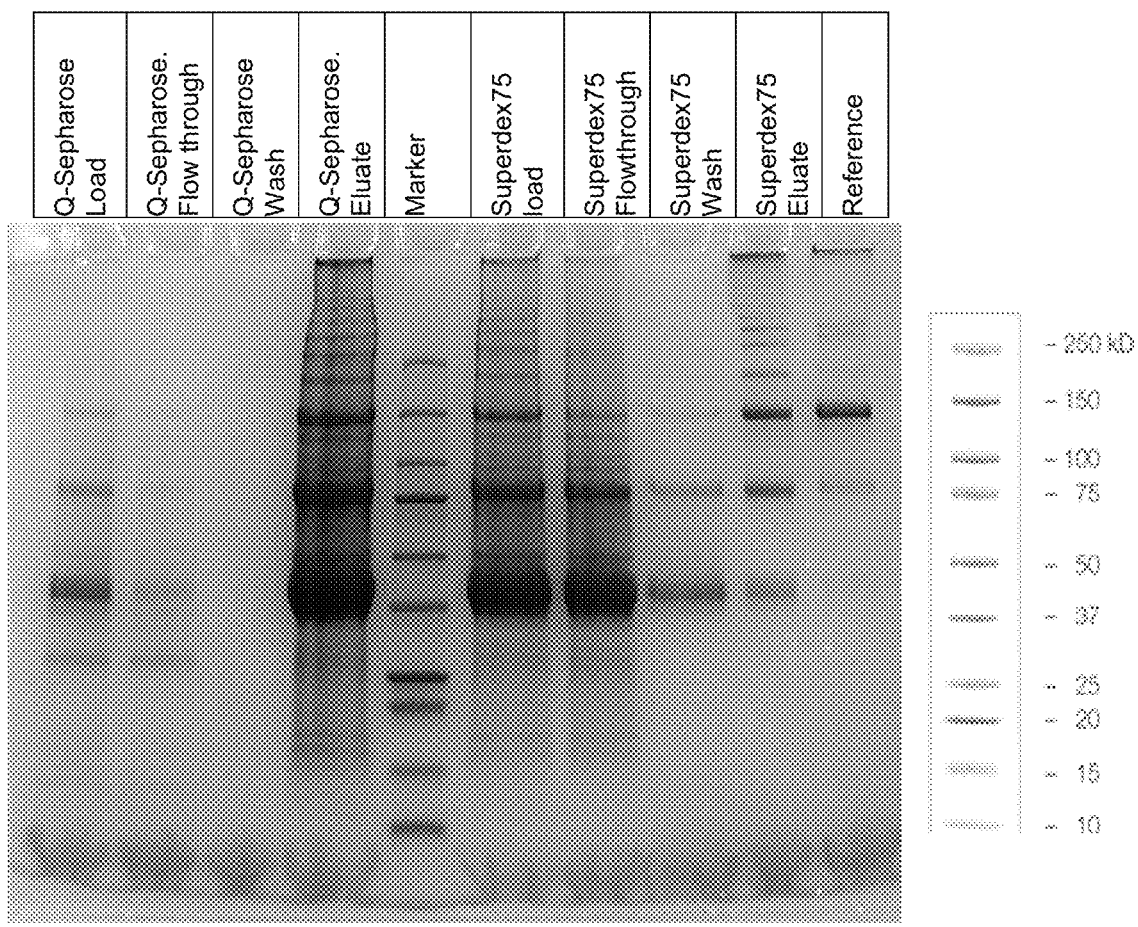
FIG. 5 is a photograph of a SDS-PAGE gel stained with Coomassie blue, showing proteins in various stages of rhSP-D purification from expressing cells.

The Superdex eluate contained SP-D in >90% purity as determined by non-reducing SDS-PAGE following Coomassie blue staining (FIG. 5). In FIG. 5, bands greater than 150 kD include higher order oligomers from SP-D. The eluate from the Superdex column was dialysed at 4° C. against a 5 mM Histidine pH 7.0 buffer containing 200 mM NaCl and 1mM EDTA prior to storage and analysis.

Example 5

Activity of SP-D in a Bacterial Aggregation Assay

The activity of SP-D purified from the clone H9D8-P1315-2A5 was tested in a bacterial aggregation assay. The bacterial aggregation assay was performed by a method substantially similar to the following method. E. coli (ATCC: Y1088) was streaked onto a bacterial agar plate and incubated at 37° C. overnight. A single colony was selected and used to inoculate an overnight culture, shaken at 37° C. overnight. A 1 mL bacterial culture was pipetted into four 1.5 mL centrifuge tubes and centrifuged at 4,000 rpm for 5 minutes. The supernatant was discarded, and the pellet resuspended in 1 mL buffer, (150 mM HEPES, 20 mM NaCl pH 7.4). The tubes were centrifuged at 4,000 rpm for 5 minutes and the pellet was resuspended in 7 mL buffer. Absorbance of the bacterial suspension was measured in a spectrometer at 700 nm. The bacterial suspension was adjusted to obtain an Absorbance in the range of 1.0000 to 1.1000. 1 M $CaCl_2$ was added to the suspension to obtain a final concentration of 5 mM $CaCl_2$. rhSP-D dilutions in placebo buffer (15 μl total volume for each dilution) were created at the following concentrations: 5, 1, 0.5, 0.25, 0.1, 0 μg/ml and added to cuvettes each containing 20 μL of the HEPES-NaCl buffer. 600 μL bacterial suspension were then added to cuvettes, and absorbance was measured every 2.5 minutes for each cuvette at 700 nm, for a total of 120 minutes.

Figure 6:
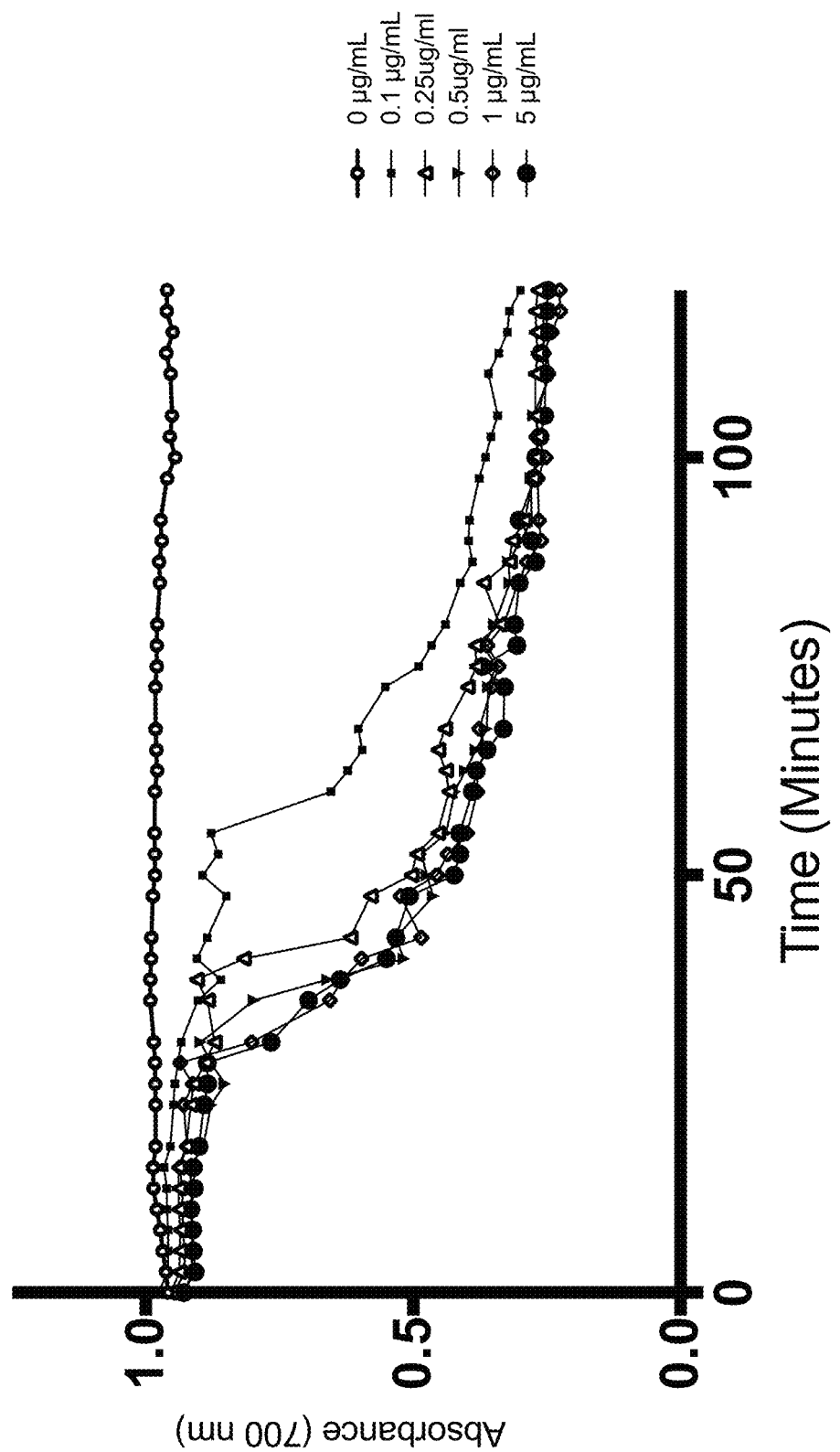
FIG. 6 is a line graph for a bacterial aggregation assay where bacteria were treated with various concentrations of rhSP-D purified from clone H9D8-P1315-2A5 to show how the SP-D treatment affected bacterial aggregation over time.

In the aggregation assay, active SP-D aggregates bacterial cells and reduces absorbance/increases transmission through the bacterial suspension. FIG. 6 shows that rhSP-D purified from the clone, H9D8-P1315-2A5 was determined to have activity in the bacterial aggregation assay. The experiment was repeated two additional times with similar results.

Human SP-D recombinantly expressed in further clones of H9D8 produced as described in example 2, above, was also analyzed for its activity. SP-D from all of the final selected clones tested had a similar high activity. One exemplary isolated clone is NM-H9D8(8B11) which was also used in subsequent analyses. NM-H9D8(8B11) has been deposited as "AT100-rhSP-D-H9D8-P20011-8B11" with the "DSMZ-Deutsche Sammlung von Mikroorganismen and Zellkulturen GmbH" in Braunschweig (Germany) by Airway Therapeutics LLC, Cincinnati, Ohio, USA on Sep. 4, 2018 from which the deposited clone can be readily identified, and an under the accession number can be readily obtained.

Example 6

Activity of SP-D in a TLR4 Inhibition Assay

Oligomeric forms of SP-D inhibit lipopolysaccharide (LPS)-induced inflammatory cell responses by preventing LPS from binding/activating the Toll-like receptor 4 (TLR4). See e.g., Yamazoe M. et al., (2008) J. Biological Chem. 283:35878-35888, which is incorporated by reference in its entirety.

Figure 7:
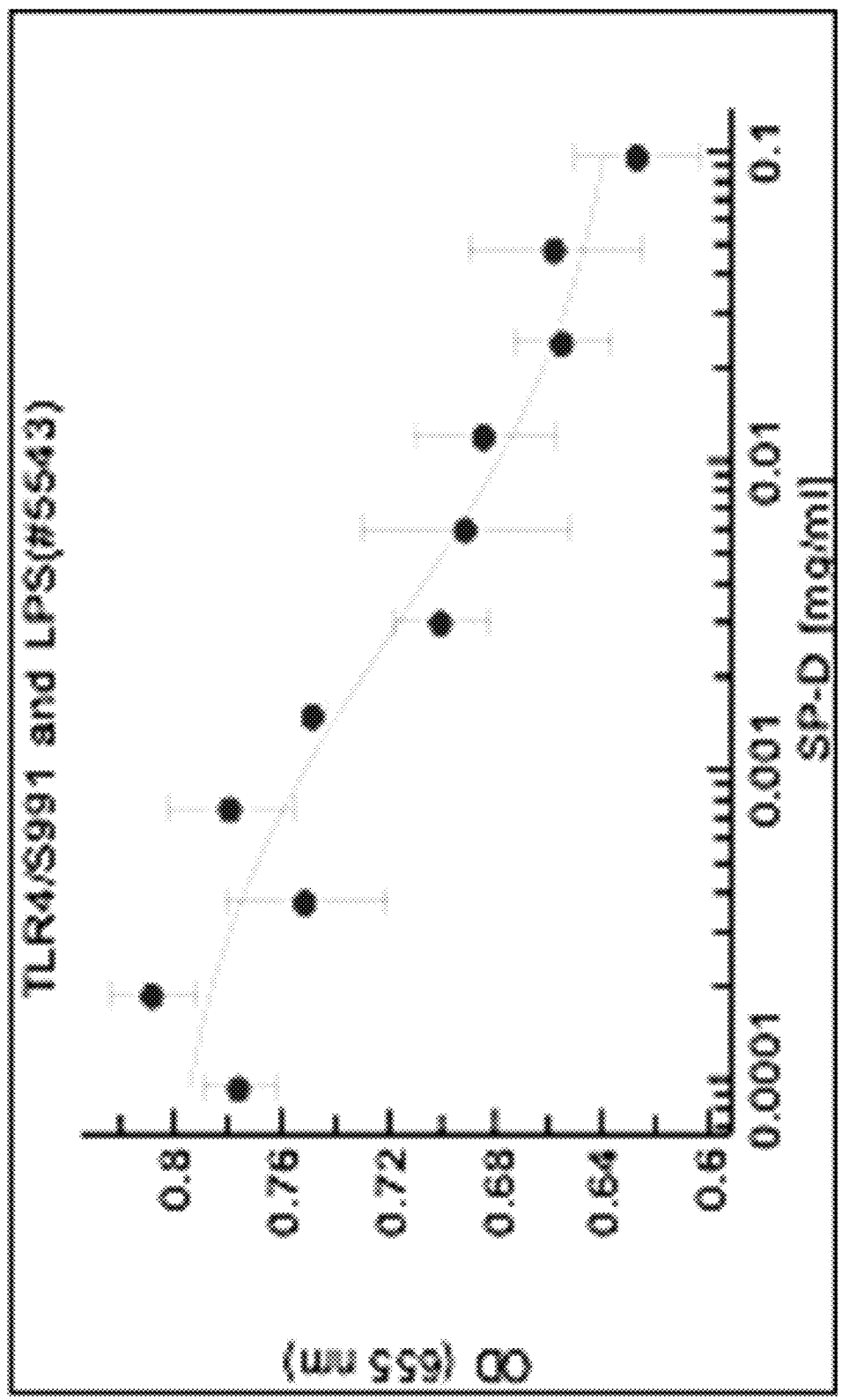
FIG. 7 is a line graph showing the inhibitory activity of increasing concentrations of rhSP-D purified from clone H9D8-P1315-2A5 in a TLR4 receptor pathway assay.

The activity of rhSP-D purified from the clone H9D8-P1315-2A5 to inhibit activation of the TLR4 pathway by LPS was tested. HEK-Blue™ hTLR4 cells (InvivoGen, San Diego, Calif., U.S.A.) were plated at a density ~20000 cells/well in 384-well plates and incubated with various concentrations of SP-D for 2 hours at 37° C., 5% CO2. LPS (Escherichia coli O26:B6, L5543 Sigma Aldrich) at an $EC_{80}$ concentration was added to each well, and the cells incubated for another 22 hours at 37° C., 5% $CO_2$. TLR4 activity was measured by detaching the cells from the wells, washing the suspended cells, resuspending the cells in PBS and removing any clumps by gentle pipetting. Washed cells were transferred to a 384-well plate at a density of $20e10^3$ cells/well containing HEK blue detection medium (InvivoGen, San Diego, Calif., U.S.A.) that had been made up in endotoxin-free water containing 5 mM $CaCl_2$ and 1% (v/v) BSA. Cells were incubated at 37° C. in 5% $CO_2$ for 24 hours, and activity of TLR4 was determined by measuring the activity of a secreted embryonic alkaline phosphatase (SEAP) reporter gene using a spectrophotometer at 655 nm. An $IC_{50}$ value for the SP-D was determined using nonlinear regression analysis by fitting the data to the four-parameter logistics equation with XLfit from idbs. FIG. 7 shows that SP-D purified from the clone, H9D8-P1315-2A5, was determined to have activity to inhibit activation of the TLR4 pathway by LPS with an $IC_{50}$ of 0.00294 mg/ml, and confirmed that the SP-D was in an active oligomeric form for such activity. Because only the logarithm of the $IC_{50}$ values are normally distributed, for the purposes of averaging numbers from a series of experiments, the $pIC_{50}$ values were used, defined as the $-Log_{10}(IC_{50})$. The experiment was repeated two additional times with similar results yielding an average $pIC_{50}$ of 2.33±0.10 mg/ml (N=3), corresponding to an average $IC_{50}$ of 0.00468 mg/ml. Human SP-D recombinantly expressed in further clones of H9D8 produced as described in example 2, above, was also analyzed for its activity in the TLR-4 assay. SP-D from all of the final selected clones tested had a similar high activity. One exemplary isolated clone is NM-H9D8(8B11) which was also used in subsequent analyses.

Example 7

Stability of SP-D from Various Sources

The stability of rhSP-D from various sources was determined. The sources included rhSP-D expressed with a wild-type SP-D leader polypeptide in H9D8 cells ("rhSP-D:WT"), and rhSP-D expressed with a TCR leader polypeptide in H9D8 cells ("rhSP-D:TCR"). Solutions of rhSP-D:WT or rhSP-D:TCR in various buffers (Buffers: 1, 2, 3, or 4) were incubated at 5° C. for several weeks. The stability of rhSP-D:WT or rhSP-D:TCR in the various buffers was determined by measuring the relative distribution of rhSP-D oligomeric forms including: rhSP-D trimers/hexamers, dodecamers, higher order oligomers "fuzzy balls", and very high order oligomers/aggregates. The relative distribution of rhSP-D oligomeric forms was determined by an asymmetric flow field-flow fractionation (AF4) with multi-angle light scattering (AF4-MALS) analysis using methods substantially the same as those provided in EXAMPLE 8. A mean result was determined from triplicate determinations, and +/− standard deviations were determined. The results are summarized in TABLE 4.

TABLE 4

| SP-D source (buffer) | Time at 5° C. (weeks) | Relative distribution of oligomeric forms (%) | | | |
|---|---|---|---|---|---|
| | | Trimer/hexamer | Dodecamer | Transition to 'Fuzzy balls' | Very high order oligomers |
| rhSP-D: TCR (1) | 0 | 17.30 ± 0.61 | 53.56 ± 2.23 | 24.19 ± 1.16 | 5.06 ± 0.63 |
| | 2 | 15.69 ± 0.75 | 58.09 ± 0.22 | 11.83 ± 0.47 | 14.89 ± 0.54 |
| | 4 | 15.92 ± 3.68 | 42.82 ± 2.62 | 14.96 ± 1.13 | 26.29 ± 1.21 |
| | 8 | 11.45 ± 0.55 | 51.57 ± 0.27 | 21.38 ± 1.39 | 15.79 ± 1.09 |

TABLE 4-continued

| SP-D source (buffer) | Time at 5° C. (weeks) | Relative distribution of oligomeric forms (%) | | | |
|---|---|---|---|---|---|
| | | Trimer/ hexamer | Dodecamer | Transition to 'Fuzzy balls' | Very high order oligomers |
| rhSP-D: TCR (2) | 0 | 13.71 ± 1.42 | 58.48 ± 0.90 | 16.06 ± 1.12 | 11.75 ± 0.60 |
| | 2 | 14.05 ± 1.99 | 61.01 ± 1.12 | 12.05 ± 1.23 | 12.88 ± 0.76 |
| | 4 | 16.39 ± 1.68 | 32.28 ± 0.27 | 24.72 ± 0.35 | 26.51 ± 1.69 |
| | 8 | 8.04 ± 0.83 | 47.40 ± 2.19 | 13.35 ± 1.54 | 31.21 ± 1.30 |
| rhSP-D: TCR (3) | 0 | 14.46 ± 0.90 | 64.06 ± 2.30 | 15.17 ± 0.90 | 6.31 ± 2.32 |
| | 2 | 13.57 ± 1.81 | 63.91 ± 0.54 | 11.11 ± 0.76 | 11.41 ± 0.68 |
| | 4 | 9.41 ± 0.70 | 56.74 ± 2.49 | 15.77 ± 3.56 | 18.08 ± 2.30 |
| | 8 | 18.22 ± 3.48 | 59.07 ± 2.45 | 11.71 ± 1.85 | 11.06 ± 1.26 |
| rhSP-D: TCR (4) | 0 | 12.49 ± 0.45 | 60.76 ± 0.58 | 13.92 ± 0.21 | 12.83 ± 0.33 |
| | 2 | 6.53 ± 1.16 | 60.60 ± 0.44 | 13.48 ± 0.30 | 19.38 ± 1.16 |
| | 4 | 9.15 ± 0.67 | 46.93 ± 0.33 | 12.45 ± 0.31 | 31.47 ± 0.53 |
| | 8 | 13.48 ± 0.32 | 52.32 ± 0.70 | 13.33 ± 0.40 | 20.87 ± 0.72 |
| rhSP-D: WT (1) | 0 | 10.21 ± 2.34 | 49.54 ± 7.07 | 16.75 ± 6.40 | 23.50 ± 5.60 |
| | 2 | 10.61 ± 0.95 | 62.05 ± 0.14 | 21.24 ± 0.84 | 6.10 ± 0.64 |
| | 4 | 9.50 ± 0.60 | 60.11 ± 0.29 | 21.37 ± 0.54 | 9.01 ± 0.14 |
| | 8 | 13.80 ± 0.48 | 59.05 ± 1.49 | 20.15 ± 1.56 | 7.00 ± 0.38 |
| rhSP-D: WT (2) | 0 | 9.12 ± 1.72 | 65.67 ± 5.02 | 18.25 ± 3.12 | 6.95 ± 3.58 |
| | 2 | 9.05 ± 0.85 | 69.20 ± 0.64 | 16.31 ± 1.00 | 5.44 ± 0.67 |
| | 4 | 9.79 ± 0.71 | 62.43 ± 0.88 | 19.91 ± 0.96 | 7.87 ± 0.56 |
| | 8 | 9.73 ± 1.23 | 67.58 ± 1.31 | 16.58 ± 1.86 | 5.70 ± 0.51 |
| rhSP-D: WT (3) | 0 | 8.81 ± 2.06 | 69.36 ± 2.27 | 17.18 ± 0.23 | 4.65 ± 0.17 |
| | 2 | 7.62 ± 0.76 | 69.28 ± 1.54 | 19.41 ± 1.67 | 3.69 ± 0.64 |
| | 4 | 9.21 ± 0.58 | 65.79 ± 1.56 | 19.96 ± 1.22 | 5.04 ± 0.93 |
| | 8 | 12.00 ± 0.82 | 66.32 ± 0.32 | 17.39 ± 0.92 | 4.30 ± 0.21 |
| rhSP-D: WT (4) | 0 | 8.58 ± 0.51 | 63.43 ± 1.26 | 20.48 ± 0.69 | 7.51 ± 0.07 |
| | 2 | 5.15 ± 0.61 | 61.56 ± 0.57 | 22.21 ± 0.48 | 11.07 ± 0.14 |
| | 4 | 9.57 ± 0.43 | 62.52 ± 0.58 | 18.82 ± 0.56 | 9.13 ± 0.42 |
| | 8 | 13.84 ± 0.02 | 63.01 ± 0.33 | 14.16 ± 0.03 | 9.00 ± 0.32 |

TABLE 4 illustrates differences in the relative stabilities of the various oligomeric forms in different solutions containing rhSP-D:WT and rhSP-D:TCR. For example, with regard to the very high order oligomeric forms of SP-D, solutions of rhSP-D:WT generally had a lower percentage of such oligomers than corresponding solutions of rhSP-D:TCR. In addition, the percentage of very high order oligomers for solutions of rhSP-D:WT did not increase substantially between at least 0 week and 2 weeks, compared to corresponding solutions of rhSP-D:TCR. With regard to dodecamer oligomeric forms of rhSP-D, the percentage of such oligomers in solutions of rhSP-D:WT were generally stable between weeks 0 and 8; in contrast; the percentage of such oligomers in solutions of rhSP-D:TCR decreased between weeks 0 and 8 in corresponding solutions.

These differences between solutions of rhSP-D:WT and rhSP-D:TCR were notable because both SP-D polypeptides have the same amino acid sequence and are each produced by H9D8 cells. rhSP-D:WT is initially expressed with a leader/signal polypeptide that corresponds with the leader/signal polypeptide of the wild-type human SP-D protein, and rhSP-D:TCR is initially expressed with a leader/signal polypeptide that corresponds with the leader/signal polypeptide of the human TCR protein. Each leader/signal sequence would have been cleaved from the corresponding protein shortly after or during translocation. This finding may be particularly advantageous for the production and development of stable solutions of human SP-D for the treatment of various lung disorders, especially solutions having the more active dodecamer oligomeric forms of SP-D.

Example 8

AF4-MALS Analysis

An asymmetric flow field-flow fractionation with multi-angle light scattering (AF4-MALS) analysis was used to determine the relative distribution of different oligomeric forms of SP-D in a solution. AF4-MALS is a separation technique related to field flow fractionation (FFF). Unlike FFF, AF4-MALS includes a single permeable wall such that a cross-flow is caused only by a carrier liquid. The cross-flow is induced by the carrier liquid constantly exiting by way of a semi-permeable wall on the bottom of a channel.

Samples were analyzed using an AF4-MALS system (Eclipse Dual Tec, Wyatt Technology Corp., Santa Barbara, Calif.) followed by UV (Ultimate 3000 variable wavelength detector, Dionex Corporation, Sunnyvale, Calif.) and MALS analysis (Dawn Heleos II detector, Wyatt Technology Corp., Santa Barbara, Calif.). A Dionex Ultimate 3000 HPLC system (Dionex Corporation, Sunnyvale, Calif.) was used to inject the samples and deliver the mobile phase to the AF4 system. The AF4 configuration used a short channel with a 350 μm thick spacer (Wyatt Technology Corp., Santa Barbara, Calif.). Analysis of the data and calculations were performed using Chromeleon (Dionex Corporation, Sunnyvale, Calif.) and Astra (Wyatt Technology Corp., Santa Barbara, Calif.) software. Samples included rhSP-D purified from either H9D8 or F9 cells transfected with an expression vector encoding rhSP-D and a wild-type SP-D leader polypeptide (pHBG1Ddhfr_WT_SP-D); and H9D8 cells transfected with an expression vector encoding rhSP-D and a wild-type TCR leader polypeptide (pHBG1Ddhfr_TCR_SP-D). Samples used are listed in TABLE 5. Parameters for an AF4-MALS system with rhSP-D are shown in TABLE 6.

TABLE 5

| Batch | Parent cell line | Expression construct | Volume (mL) |
|---|---|---|---|
| S729 | H9D8 | pHBG1Ddhfr_TCR_SP-D | 0.25 |
| S730 | F9 | pHBG1Ddhfr_WT_SP-D | 0.25 |

TABLE 5-continued

| Batch | Parent cell line | Expression construct | Volume (mL) |
|---|---|---|---|
| S731 | H9D8 | pHBG1Ddhfr_WT_SP-D | 0.25 |

TABLE 6

| Step | Start time (min) | End time (min) | Duration (min) | Mode | X flow start (ml/min) | X flow end (ml/min) |
|---|---|---|---|---|---|---|
| 1 | 0 | 1 | 1 | Focus | | |
| 2 | 1 | 2 | 1 | Focus + inject | | |
| 3 | 2 | 3.5 | 1.5 | Focus | | |
| 4 | 3.5 | 3.7 | 0.2 | Elution | 0.5 | 3 |
| 5 | 3.7 | 6.7 | 3 | Elution | 3 | 3 |
| 6 | 6.7 | 16.7 | 10 | Elution | 3 | 0.18 |
| 7 | 16.7 | 26.7 | 10 | Elution | 0.18 | 0.18 |
| 8 | 26.7 | 41.7 | 15 | Elution | 0.18 | 0 |
| 9 | 41.7 | 51.7 | 10 | Elution | 0 | 0 |
| 10 | 51.7 | 56.7 | 5 | Elution + Inject | 0 | 0 |
| 11 | 56.7 | 57 | 0.3 | Elution | 0 | 0 |

Detector Flow: 0.5 ml/min
Inject Flow: 0.2 ml/min
Focus Flow: 0.5 ml/min
Injection Amount: 5 µg
Mobile phase: 20 mM Tris, 200 mM NaCl, pH 7.4
Channel: short (145 mm)
Spacer: 350 µM
Membrane: 10 kD PES Data using AF4-MALS was collected using a UV detector and a multi-angle light-scattering detector and analyzed to determine absolute molar mass and size of SP-D at a certain time during elution. The ratio of size to mass was indicative of the shape of the SP-D. From the size to mass ratio, it was determined that in the early stages of an elution (0-34 minutes) the SP-D molecule had a linear or rod-shape. For rod model calculations, the software assumed that the thickness of a rod-shaped particle was insignificant (0.0 nm) compared to its length. If the thickness was significant, its thickness or approximate thickness in nm is used. Rod thickness was estimated from atomic force microscopy (AFM) data, and rod lengths were determined to be consistent with AFM measurements of 136±8.1 nm (R. Arroyo et al., J Mol Biol (2018) 430: 1495-1509). The later stages of the elution (34-45 minutes) for SP-D indicated that a more compact structure was being observed. A second order Debye model was employed for analysis of these stages of the elution. The second order Debye model provided better results over a wider range of molar masses, including the very large (greater than ~10e6 Daltons or ~50 nm RMS radius). For dodecamer oligomeric forms of SP-D, molecular weight was determined to be 520.09+/−4.61 kDa (N=72 determinations).

A first peak in the elution profile (Peak 1) contained SP-D trimers and hexamers based on mass calculations according to the rod model. A second peak in the elution profile (Peak 2) contained SP-D dodecamers. A third peak in the elution profile (Peak 3) contained intermediate species between SP-D dodecamers to SP-D 'fuzzy balls' based on the intermediate MW as determined by the rod model. A fourth peak in the elution profile (Peak 4) contained a heterogeneous mass of SP-D oligomers with constant RMS radius of about 70 nm, consistent with what has been observed by AFM measurements for the fuzzy ball species. Beyond 36 minutes in the elution profile the RMS radius increases, indicative of aggregate species.

Example 9

N-glycan Profiling

The N-glycosylation patterns of SP-D produced in NM-H9D8 cells (rhSP-D), and SP-D obtained from human amniotic fluid (hSP-D) were compared. The purified SP-D protein was denatured and reduced. N-glycans were released by action of N-glycanase F. Free N-glycans were tagged with a fluorophore at the reducing end, followed by a purification step employing solid phase extraction. The mixture of purified fluorescence tagged N-glycans was applied to hydrophilic interaction ultra-performance chromatography with fluorescence detection (HILIC-UPLC-FLD) coupled to electrospray ionization quadrupole time-of-flight tandem mass spectrometry (ESI-Q-TOF MS/MS). Glycans were quantified by fluorescence peak areas and identified by molecular masses in combination with fragment analyses.

Fluorescence traces showed a constant retention time range for all N-glycans. Reliable structure assignment was performed through MS/MS experiments due to consistent signals throughout all samples. The glycosylation patterns of the compared SP-D proteins are shown in TABLE 7.

TABLE 7

| N-glycan | Percentage of carbohydrate structures including the N-glycan | |
|---|---|---|
| | hSP-D | rhSP-D |
| fucosylated glycan | 91 | 99 |
| glycan with bisecting N-acetylglucosamine | 18 | 38 |
| glycan with at least one sialic acid | 52 | 58 |
| glycan with 1 sialic acid | 45 | 50 |
| glycan with 2 sialic acids | 7 | 8 |
| glycan with 3 sialic acids | 0 | 0 |
| glycan with at least one galactose | 93 | 92 |
| glycan with 1 galactose | 19 | 22 |
| glycan with 2 galactoses | 64 | 66 |
| glycan with 3 galactoses | 10 | 4 |
| monoantennary glycan | 1 | 1 |
| biantennary glycan | 82 | 90 |
| triantennary glycan | 13 | 5 |
| tetraantennary glycan | 1 | 1 |
| glycan with at least one GalNAc | 1 | 11 |
| hybrid-type glycan | 2 | 2 |
| high mannose-type glycan | 2 | 2 |

From the amount of the different antennarities, the A-number can be calculated as a measure of the overall antennarity using the formula 1×percent monoantennary glycans+2×percent biantennary glycans+3×percent triantennary glycans+4×percent tetraantennary glycans=A-number. The A-numbers of rhSP-D and hSP-D are very similar with rhSP-D having an A-number of 200 and hSP-D having an A-number of 208.

In some aspects, the N-glycosylation profiles of hSP-D and of rhSP-D were similar. For example, for both hSP-D and rhSP-D the percentage of carbohydrate structures including a glycan with 3 sialic acids, a monoantennary glycan, a tetraantennary glycan, a hybrid-type glycan, or a high mannose-type glycan, were the same. However, in some aspects, the N-glycosylation profiles of hSP-D and rhSP-D were dissimilar. For example, the percentage of carbohydrate structures including a glycan with bisecting N-acetylglucosamine, a glycan with 1 sialic acid, a glycan with 3 galactoses, a triantennary glycan, or a glycan with at least one GalNA, were different between the hSP-D and of SP-D.

Figure 8:
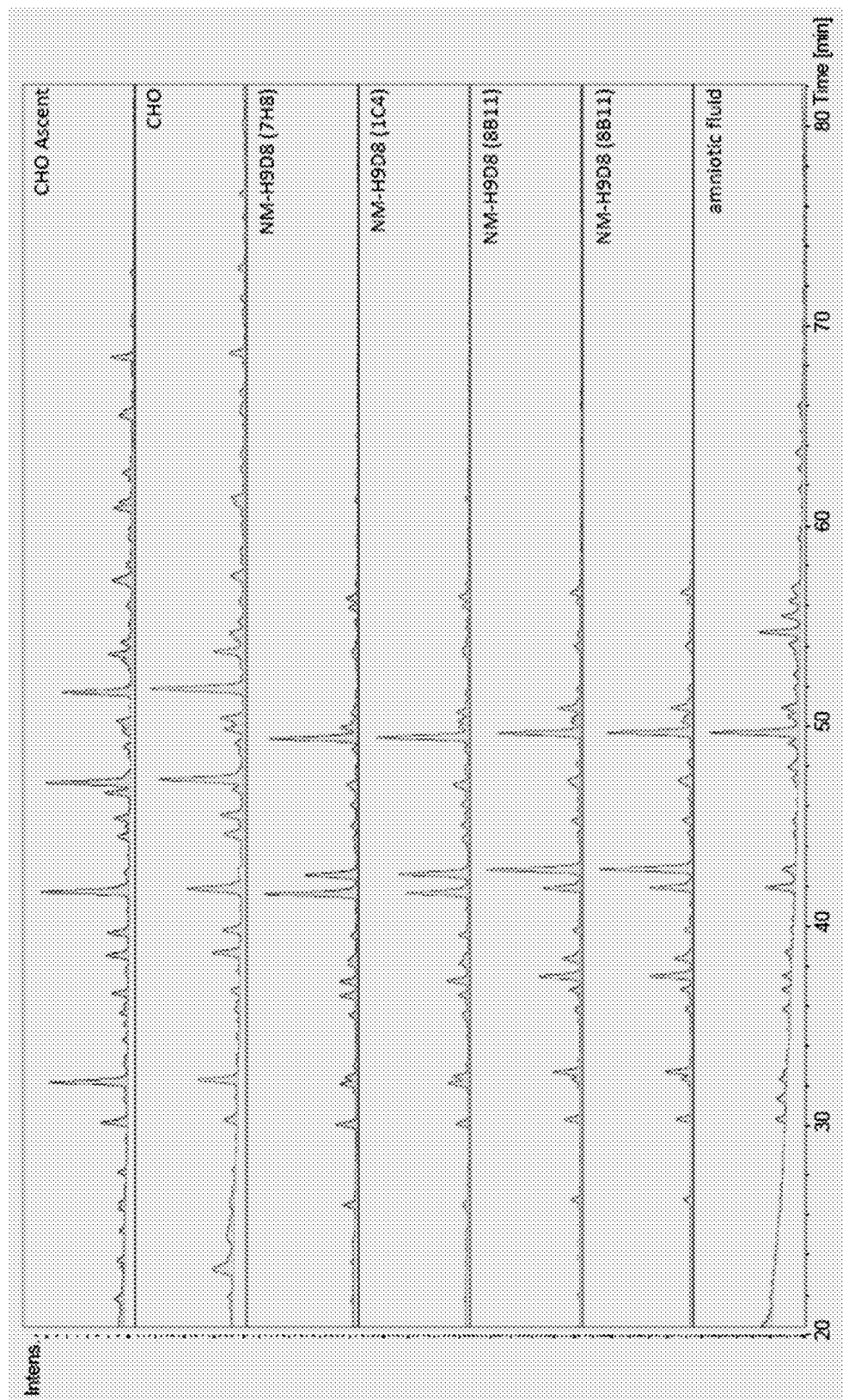
FIG. 8 is a chromatogram of fluorescence tagged N-glycans released from purified rhSP-D of different sources and subjected to hydrophilic interaction ultra-performance chromatography with fluorescence detection.
Figure 9:
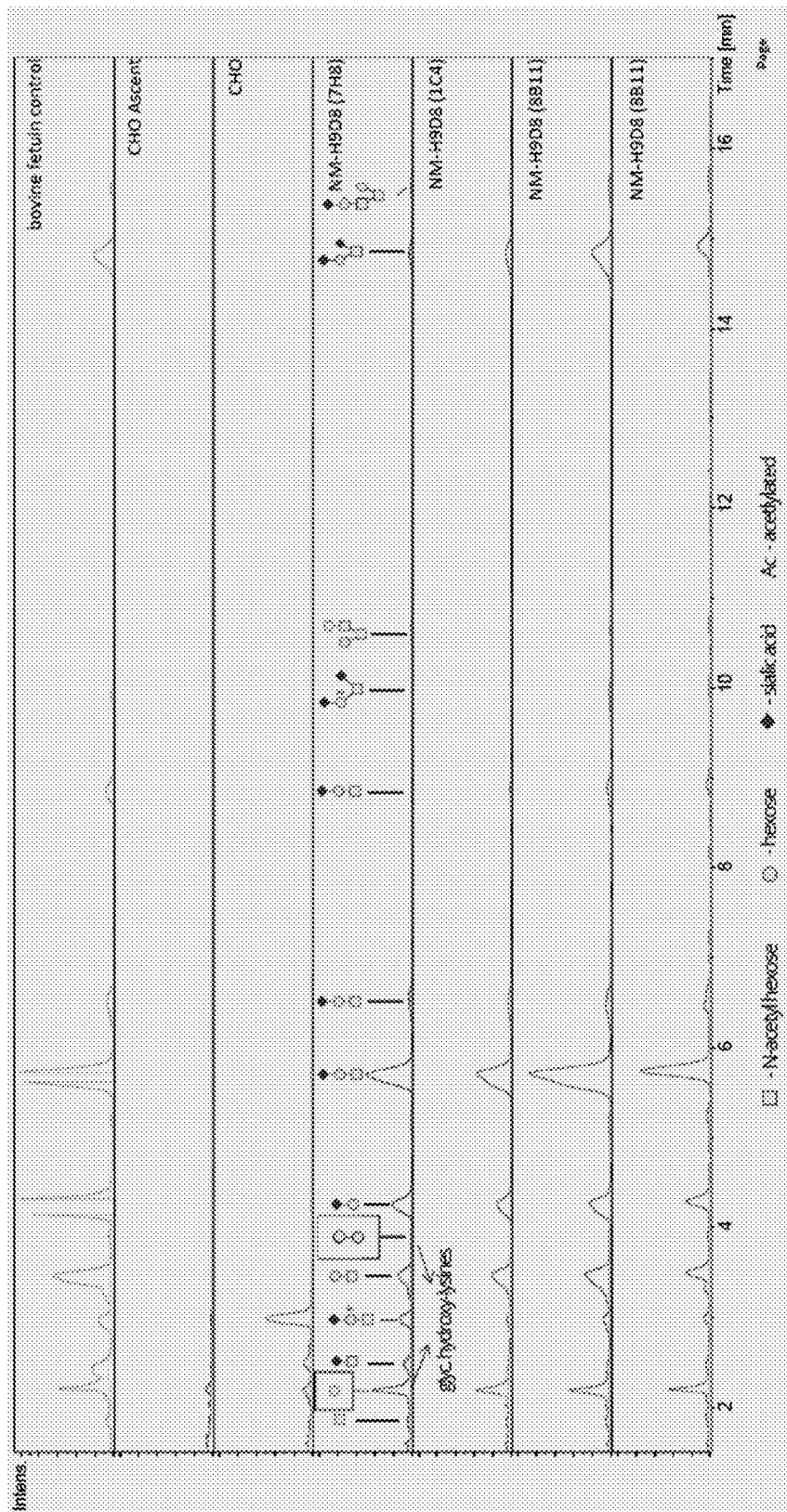
FIG. 9 is a chromatogram of fluorescence tagged O-glycans released from SP-D of different sources and subjected to hydrophilic interaction ultra-performance chromatography with fluorescence detection.

In a further analysis, the glycoprofiles of recombinant human SP-D produced in different clones of NM-H9D8 cells (rhSP-D), including two different purification batches from the NM-H9D8(8B11) clone, recombinant human SP-D produced in different clones of CHO cells (CHO-SP-D), and native SP-D obtained from human amniotic fluid (hSP-D) were compared. As shown in FIG. 8, the N-glycosylation profile of rhSP-D and hSP-D is highly comparable, while CHO-SP-D shows remarkable differences due to the production in a non-human cell line. FIG. 9 further demonstrates that also the O-glycosylation profiles of NM-H9D8-derived rhSP-D and CHO-derived CHO-SP-D differ significantly. O-glycosylation of SP-D obtained from human amniotic fluid could not be determined due to the high amount of protein necessary for this analysis. The N-glycosylation profile includes all glycan structures attached to asparagine residues of the polypeptide chain of SP-D while the O-glycosylation profile shows the glycan structures attached to serine, threonine, hydroxy-lysine and hydroxy-proline residues. In conclusion, rhSP-D produced in clones of NM-H9D8 cells has a human glycosylation pattern which closely resembles the glycosylation of naturally occurring hSP-D.

In addition, the linkage of the sialic acids (N-acetyl-neuraminic acid; NANA) in the glycan structures of SP-D was analyzed. NANA generally may be linked in an α2,3 or an α2,6 conformation to the terminal galactose residue. In human glycosylation, a mixture of α2,3- and α2,6-linked NANA is found, while hamster cells such as CHO do not produce α2,6-linked NANA. CHO as well as NM-H9D8 produced human SP-D was purified, denatured and reduced. N-Glycans were released during incubation with N-glycanase F. Free N-glycans were labeled with a fluorophore (RapiFluor, Waters) followed by purification step employing a HILIC solid phase extraction. For neuraminidase treatment, purified N-glycans were digested with neuraminidase S (NEB) for 1 h at 37° C. Neuraminidase S specifically removes α2,3-linked NANA while it does not cleave off α2,6-linked NANA. The enzyme was removed through repeated HILIC solid phase extraction. An I-class system with fluorescence detection (Waters) was used for HILIC-UPLC. The mixture of purified fluorescence tagged N-glycans were separated on an Acquity UPLC BEH Glycan column (150×2.1 mm, 1.7 u, Waters) at 60° C. with a flowrate of 0.5 mL/min. 100% acetonitrile (A) and 100 mM ammoniumformiate, pH4.5, were used as the eluent system and the gradient of 22% B to 44% B in 82 min was applied.

The fluorescence wavelength settings were: $\lambda_{ex}$ 265 nm and $\lambda_{em}$ 425 nm. A coupled Bruker Impact HD ESI-Q-TOF-MS (MS) was used for N-glycan identification in positive ion mode. N-glycans were identified according to molecular masses in combination with fragment analyses.

Figure 10:
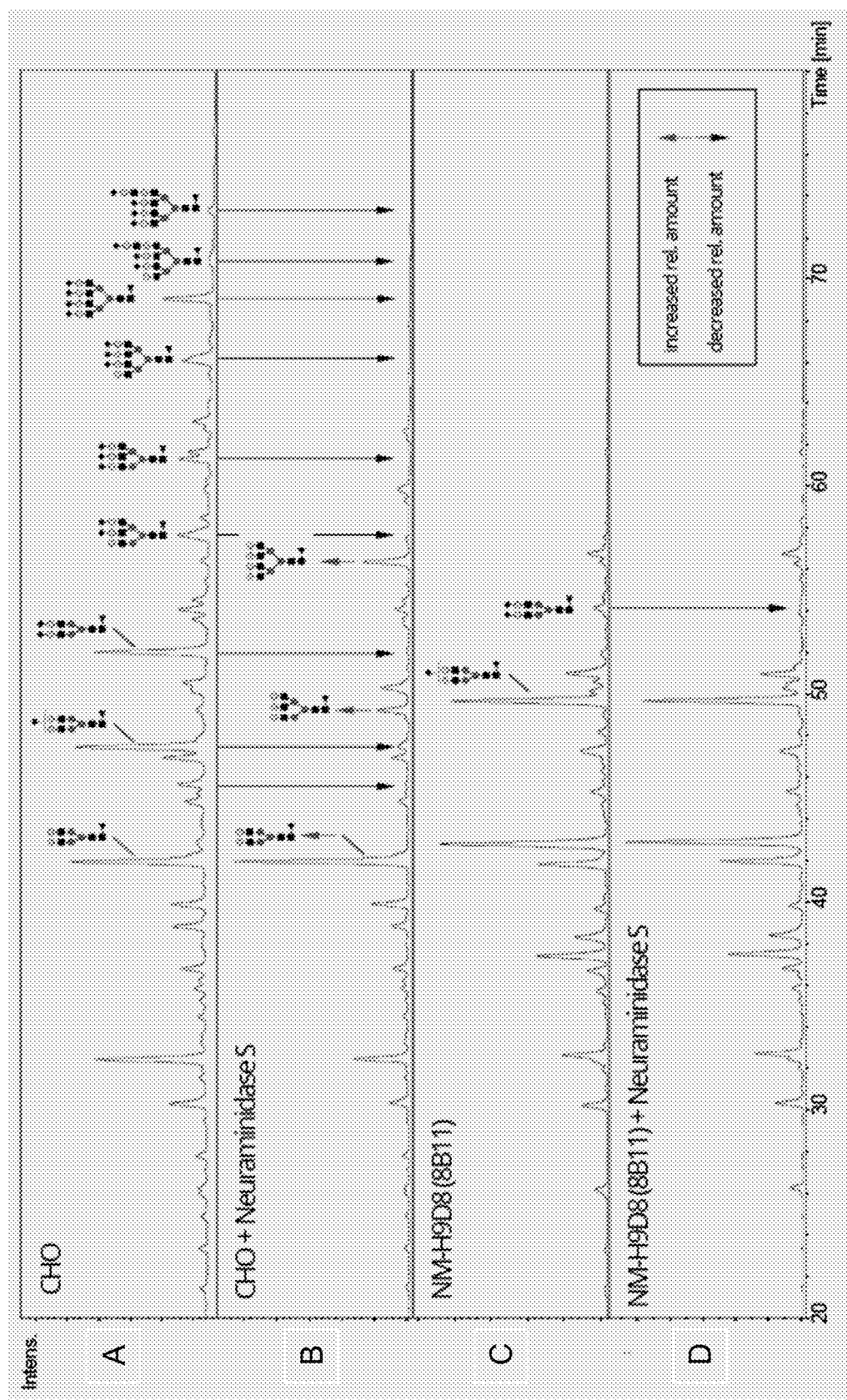
FIG. 10 is a chromatogram of fluorescence tagged N-glycans released from SP-D of produced in CHO (panels A, and B) and NM-H9D8(8B11) (panels C, and D), without (panels A, and C) and with (panels B, and D) neuraminidase S treatment, and subjected to hydrophilic interaction ultra-performance chromatography with fluorescence detection.

The analysis revealed that SP-D from CHO shows a heterogeneous N-glycan profile between 20 and 70 min RT. Besides the three major peaks comprising biantennary N-glycans with zero (S0), one (S1) and two (S2) NANAs, higher antennary structures with up to four NANAs are detected between 53-70 min. The biantennary S1 and S2 structures as well as most of the higher antennary structures after 56 min RT are affected by neuraminidase S treatment proving the presence of 2,3-linked NANA. The overall sialylation was strongly reduced, indicating the presence of mainly α2,3-linked NANA in CHO-produced SP-D (see FIG. 10, panels A and B). In SP-D from NM-H9D8(8B11) cells only slight changes in the N-glycoprofile were detected after neuraminidase treatment. The monosialylated peak at RT 50 min is not affected by neuraminidase S treatment. Only one minor peak change comprising an S2 N-glycan in SP-D from NM-H9D8 at RT 54 min was observed. The overall sialylation was only slightly reduced by neuraminidase S, indicating that SP-D produced in NM-H9D8(8B11) comprises mainly α2,6-linked NANA and only minor amounts of α2,3-linked NANA (see FIG. 10, panels C and D).

The term "comprising" as used herein is synonymous with "including," "containing," or "characterized by," and is inclusive or open-ended and does not exclude additional, unrecited elements or method steps.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it covers all modifications and alternatives coming within the true scope and spirit of the invention.

All references cited herein, including but not limited to published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

What is claimed is:

1. A method for producing a human surfactant protein D (SP-D) polypeptide composition comprising:
   (a) introducing a polynucleotide encoding the SP-D polypeptide into a human cell selected from the group consisting of: NM-H9D8, NM-H9D8-E6Q12, NM-H9D8(8B11), and NM-F9;
   (b) culturing the cell under conditions in which the SP-D polypeptide is expressed; and
   (c) isolating the expressed SP-D polypeptide from the cell, wherein the expressed SP-D polypeptide comprises a glycosylation pattern substantially similar to a glycosylation pattern of a naturally-occurring human SP-D,
   wherein the expressed SP-D polypeptide and the naturally-occurring human SP-D each comprise the same percentage of carbohydrate structures comprising: (i) a glycan with 3 sialic acids, (ii) a monoantennary glycan, (iii) a tetraantennary glycan, (iv) a hybrid-type glycan, or (v) a high mannose-type glycan.

2. The method of claim 1, wherein the cell is a NM-H9D8 cell.

3. The method of claim 1, wherein the cell is a NM-H9D8 (8B11) cell.

4. The method of claim 1, wherein the polynucleotide encodes a leader polypeptide selected from a wild type SP-D polypeptide leader sequence, and a wild type T-cell receptor (TCR) polypeptide leader sequence.

5. The method of claim 4, wherein the leader polypeptide comprises the amino acid sequence of SEQ ID NO:05 or SEQ ID NO:10.

6. The method of claim 1, wherein the polynucleotide encodes a pre-polypeptide comprising a leader polypeptide and the SP-D polypeptide, the pre-polypeptide having an amino acid sequence comprising SEQ ID NO:04 or SEQ ID NO:09.

7. The method of claim 1, wherein the SP-D polypeptide comprises a residue at a polymorphic position, wherein the residue is selected from the group consisting of Met11/31, Thr160/180, Ser 270/290, and Ala 286/306.

8. The method of claim 1, further comprising isolating a population of the expressed SP-D polypeptides, each expressed SP-D polypeptide comprising a complex-type carbohydrate attached at an N-glycosylation site, wherein the population has a glycosylation pattern comprising the following characteristics:
   (i) at least 70% of the complex-type carbohydrates include a core fucose;
   (ii) at least 10% of the complex-type carbohydrates include at least one sialic acid residue;
   (iii) at least 50% of the complex-type carbohydrates include at least a biantennary carbohydrate structure;
   (iv) at least 10% of the complex-type carbohydrates include a bisecting N-acetylglucosamine;
   (v) less than 10% of the carbohydrates are high-mannose type structures; and
   (vi) a detectable amount of α2,6-coupled sialic acid residues.

9. The method of claim 8, wherein the population has a glycosylation pattern comprising one or more of the following characteristics:
   (i) at least 20% of the complex-type carbohydrates include a bisecting N-acetylglucosamine; and
   (iii) at least 85% of the complex-type carbohydrates include a core fucose.

10. The method of claim 1, wherein the polynucleotide encodes a dihydrofolate reductase polypeptide, wherein culturing the cell comprises contacting the cell with an antifolate, and wherein expression of the SP-D polypeptide is increased by increasing the concentration of the antifolate.

11. The method of claim 1, wherein the cell is cultured in a perfusion bioreactor or in a continuous culture.

12. The method of claim 1, wherein culturing the cell comprises maintaining a growth medium having a pH 7.2, dissolved oxygen in a range less than 40% and greater than 20%, and temperature at 37° C.

13. The method of claim 1, wherein the polynucleotide is an expression vector encoding the SP-D polypeptide, wherein the expression vector encodes a leader polypeptide, and a dihydrofolate reductase, wherein the leader polypeptide is selected from a wild type SP-D polypeptide leader sequence or a wild type T-cell receptor (TCR) polypeptide leader sequence.

14. The method of claim 13, wherein the leader polypeptide comprises SEQ ID NO: 05 or SEQ ID NO: 10.

15. The method of claim 13, wherein the expression vector encodes a pre-polypeptide comprising the leader polypeptide and the SP-D polypeptide, the pre-polypeptide having an amino acid sequence comprising SEQ ID NO:04 or SEQ ID NO:09.

16. An immortalized human cell comprising an expression vector encoding a leader polypeptide, a human surfactant protein D (SP-D) polypeptide, and a dihydrofolate reductase, wherein the leader polypeptide is selected from a wild type SP-D polypeptide leader sequence or a wild type T-cell receptor (TCR) polypeptide leader sequence,
   wherein the cell is selected from the group consisting of NM-H9D8, NM-H9D8-E6Q12, NM-H9D8(8B11), and NM-F9, and
   wherein the cell is capable of expressing the SP-D polypeptide comprising a glycosylation pattern substantially similar to a glycosylation pattern of a naturally-occurring human SP-D,
   wherein the expressed SP-D polypeptide and the naturally-occurring human SP-D each comprise the same percentage of carbohydrate structures comprising: (i) a glycan with 3 sialic acids, (ii) a monoantennary glycan, (iii) a tetraantennary glycan, (iv) a hybrid-type glycan, or (v) a high mannose-type glycan.

17. The cell of claim 16, wherein the cell is selected from the group consisting of NM-H9D8, NM-H9D8-E6Q12, and NM-F9.

18. The cell of claim 16, wherein the cell is a NM-H9D8 cell.

19. The cell of claim 16, wherein the cell is a NM-H9D8 (8B11) cell.

20. The method of claim 1, wherein the expressed SP-D polypeptide and the naturally-occurring human SP-D each have an antennarity number within a range from 190 to 215.

* * * * *

UNITED STATES PATENT AND TRADEMARK OFFICE
CERTIFICATE OF CORRECTION

PATENT NO. : 10,752,914 B2
APPLICATION NO. : 16/121039
DATED : August 25, 2020
INVENTOR(S) : Jan Susan Rosenbaum It is certified that error appears in the above-identified patent and that said Letters Patent is hereby corrected as shown below:

On the Title Page

In Column 1, Item (73), Line 2, under Assignees, delete "Cinncinnati" and insert --Cincinnati--.

In Column 2, Item (56), Line 33, under Other Publications, delete "Seperations" and insert --Separations--.

In the Specification

In Column 1, Line 25, delete "entirety" and insert --entirety.--.

In Column 4, Line 3, delete "and or" and insert --and/or--.

In Column 11, Line 53, delete "acetylglucosymine" and insert --acetylglucosamine--.

In Columns 15-16, in table, Line 7, delete "at" and insert --ctt--.

In Columns 15-16, in table, Line 15, delete "at" and insert --ctt--.

In Columns 15-16, in table, Line 15, delete "at" and insert --ctt--.

In Columns 15-16, in table, Line 27, delete "at" and insert --ctt--.

In Columns 15-16, in table, Line 35, delete "at" and insert --ctt--.

In Columns 15-16, in table, Line 35, delete "at" and insert --ctt--.

In Column 19, Line 38, delete "docdecamer" and insert --dodecamer--.

In Column 21, Line 7, delete "Absorbance" and insert --absorbance--.

Signed and Sealed this
Tenth Day of November, 2020

Andrei Iancu
*Director of the United States Patent and Trademark Office*

CERTIFICATE OF CORRECTION (continued)
U.S. Pat. No. 10,752,914 B2

In the Claims

In Column 40, Line 3, Claim 9, delete "(iii)" and insert --(ii)--.